United States Patent
Gilmore et al.

(10) Patent No.: US 10,184,892 B2
(45) Date of Patent: Jan. 22, 2019

(54) DETERMINATION OF WATER TREATMENT PARAMETERS BASED ON ABSORBANCE AND FLUORESCENCE

(71) Applicants: Horiba Instruments Incorporated, Irvine, CA (US); Horiba Advanced Techno Co., Ltd., Kyoto (JP)

(72) Inventors: Adam Matthew Gilmore, Flemington, NJ (US); Kiichiro Tomioka, Shiga-ken (JP)

(73) Assignees: HORIBA INSTRUMENTS INCORPORATED, Irvine, CA (US); HORIBA ADVANCED TECH CO. LTD., Kyoto (JP)

( * ) Notice: Subject to any disclaimer, the term of this patent is extended or adjusted under 35 U.S.C. 154(b) by 439 days.

(21) Appl. No.: 14/527,753

(22) Filed: Oct. 29, 2014

(65) Prior Publication Data

US 2016/0123882 A1 May 5, 2016

(51) Int. Cl.
*G01N 21/64* (2006.01)
*G01N 21/33* (2006.01)
(Continued)

(52) U.S. Cl.
CPC .......... *G01N 21/645* (2013.01); *G01N 21/31* (2013.01); *G01N 21/85* (2013.01); *G01N 33/18* (2013.01);
(Continued)

(58) Field of Classification Search
CPC ...... G01N 21/645; G01N 21/64; G01N 21/63; G01N 2021/6463; G01N 2021/6484;
(Continued)

(56) References Cited

U.S. PATENT DOCUMENTS

| 3,666,362 A | 5/1972 | Chance |
| 3,917,406 A | 11/1975 | Siegler, Jr. |

(Continued)

FOREIGN PATENT DOCUMENTS

| CN | 101275905 A | 10/2008 |
| CN | 103630523 A | 3/2014 |

(Continued)

OTHER PUBLICATIONS

Kling. "Fluorometers Dissected, Fluorometry offers lower detection limits for various applications", Analytical Chemistry Mar. 1, 2000, p. 219A-224A.

(Continued)

*Primary Examiner* — John Lee
(74) *Attorney, Agent, or Firm* — Brooks Kushman P.C.

(57) ABSTRACT

A monitoring system configured to receive an on-line sample associated with a process includes a sample chamber positioned to receive the on-line sample and a detector positioned to selectively receive and detect multiple wavelengths of light transmitted through the sample during an absorbance measurement, and emitted by the sample during a fluorescence measurement in response to illumination by each of the at least one excitation wavelength. An optical fiber couples light transmitted through the sample and directs the transmitted light to the multi-channel detector during the absorbance measurement. Optics direct light emitted by the sample during the fluorescence measurement to the detector without passing through any optical fiber. A computer in communication with the detector is configured to correct the fluorescence measurement using the absorbance measurement and determine a sample parameter based on the fluorescence and absorbance measurements of the on-line sample.

15 Claims, 12 Drawing Sheets

(51) Int. Cl.
*G01N 21/85* (2006.01)
*G01N 21/31* (2006.01)
*G01N 21/84* (2006.01)
*G01N 33/18* (2006.01)

(52) U.S. Cl.
CPC ............... *G01N 2021/3155* (2013.01); *G01N 2021/6484* (2013.01); *G01N 2021/8411* (2013.01); *G01N 2201/061* (2013.01)

(58) Field of Classification Search
CPC ......... G01N 2021/8411; G01N 21/314; G01N 21/31; G01N 2021/3155; G01N 21/3103; G01N 33/18; G01N 33/1893; G01N 2201/061
See application file for complete search history.

(56) References Cited

U.S. PATENT DOCUMENTS

| | | |
|---|---|---|
| 4,279,511 A | 7/1981 | Maute et al. |
| 4,305,660 A | 12/1981 | Kallet |
| 4,475,813 A | 10/1984 | Munk |
| 4,867,559 A | 9/1989 | Bach |
| 4,927,265 A | 5/1990 | Brownlee |
| 5,285,254 A | 2/1994 | De Sa |
| 5,414,508 A | 5/1995 | Takahashi et al. |
| 6,236,456 B1 | 5/2001 | Giebeler et al. |
| 6,970,241 B1 | 11/2005 | DeSa |
| 7,209,223 B1 | 4/2007 | Hull et al. |
| 7,265,827 B2 | 9/2007 | Slutter et al. |
| 7,324,202 B2 | 1/2008 | Leonard et al. |
| 7,569,839 B2 | 8/2009 | Gilmore et al. |
| 7,595,881 B2 | 9/2009 | Leonard et al. |
| 8,901,513 B2* | 12/2014 | Gilmore ............... G01N 21/645 250/459.1 |
| 8,981,314 B2* | 3/2015 | Klinkhammer .... G01N 21/0303 250/372 |
| 2002/0104787 A1 | 8/2002 | Murayama et al. |
| 2003/0160961 A1* | 8/2003 | Hafeman .................. G01J 3/08 356/433 |
| 2004/0011965 A1* | 1/2004 | Hodgkinson .......... G01N 21/64 250/461.1 |
| 2004/0239944 A1* | 12/2004 | Shirai ..................... G01N 21/05 356/481 |
| 2005/0057753 A1 | 3/2005 | Mosley et al. |
| 2005/0089993 A1* | 4/2005 | Boccazzi ............ B01F 13/0059 435/286.2 |
| 2005/0264803 A1 | 12/2005 | Jones |
| 2007/0037135 A1 | 2/2007 | Barnes et al. |
| 2008/0030712 A1* | 2/2008 | Tokhtuev ........... G01N 21/6402 356/51 |
| 2008/0174767 A1 | 7/2008 | Leonard et al. |
| 2008/0192249 A1 | 8/2008 | Babichenko et al. |
| 2008/0272312 A1 | 11/2008 | Tuschel |
| 2008/0285036 A1* | 11/2008 | Hafeman .................. G01J 3/08 356/433 |
| 2010/0308234 A1 | 12/2010 | Harju et al. |
| 2011/0044858 A1* | 2/2011 | Jaffe ......................... G01J 3/10 422/82.08 |
| 2011/0058178 A1* | 3/2011 | Tearney ............... A61B 5/0062 356/479 |
| 2011/0260079 A1* | 10/2011 | Tokhtuev ........... G01N 21/6402 250/461.1 |
| 2012/0034702 A1 | 2/2012 | Croud et al. |
| 2012/0205547 A1 | 8/2012 | Klinkhammer et al. |
| 2012/0219029 A1* | 8/2012 | Scott ......................... G01J 3/10 372/38.02 |
| 2012/0228519 A1* | 9/2012 | Gilmore ............... G01N 21/645 250/459.1 |
| 2012/0252704 A1* | 10/2012 | Jaffe ......................... G01J 3/10 506/39 |
| 2012/0300194 A1* | 11/2012 | Zimenkov ............... G01J 3/10 356/72 |
| 2013/0020480 A1 | 1/2013 | Ford et al. |
| 2013/0083315 A1* | 4/2013 | Lo ............................. G01J 3/46 356/73 |
| 2013/0119277 A1* | 5/2013 | Atzler .................... G01N 21/64 250/459.1 |
| 2013/0308122 A1* | 11/2013 | Merchez .............. G01N 15/147 356/72 |
| 2014/0160466 A1 | 6/2014 | Muller et al. |
| 2014/0191138 A1* | 7/2014 | Atzler .................. G01N 21/645 250/458.1 |
| 2015/0041682 A1* | 2/2015 | Cano .................... G01N 21/274 250/459.1 |
| 2015/0083903 A1* | 3/2015 | Gilmore ............... G01N 21/645 250/252.1 |
| 2015/0177150 A1* | 6/2015 | Rothberg ............. C12Q 1/6869 506/2 |
| 2016/0122201 A1* | 5/2016 | Gilmore .................. C02F 1/008 700/271 |
| 2016/0123882 A1* | 5/2016 | Gilmore ............... G01N 21/645 250/227.11 |

FOREIGN PATENT DOCUMENTS

| | | |
|---|---|---|
| EP | 0616211 B1 | 1/1999 |
| JP | 2002340787 A | 11/2002 |
| JP | 2014510915 A | 5/2014 |
| WO | 9614569 | 5/1996 |
| WO | 0063680 A1 | 10/2000 |

OTHER PUBLICATIONS

Holland et al. "A Unique Computer Centered Instrument for Simultaneous Absorbance and Fluorescence Measurements", Analytical Chemistry Jan. 1973, vol. 45, No. 1, p. 145-153.
Monte et al. "Minimizing Uncertainty for Traceable Fluorescence Measurements—The BAM Reference Fluorometer", Federal Institute for Materials Research and Testing (BAM) Working Group Optical Spectroscopy, 1.3, Richard-Willstatter-Strabe 11, D-12489 Berlin, Germany. 2005, 1 Page.
"PHAR 7633 CHapter 24, Pharmaceutical Analysis, Drug Quantitation", http:www.boomer.org/c/p4/c24-c2403.html, Retrieved Dec. 9, 2010, 8 Pages.
"Fluorescence spectroscopy—Wikipedia, the free encyclopedia", http://en.wikipedia.org/wiki/Fluorescence_spectroscopy, Retrieved Dec. 9, 2010, 5 Pages.
"STAR Grant R832738: Rapid Detection of Trace Endocrine Disrupting Chemicals in Complex Mixtures: A Full-Spectrum Deconvolution Technique with a UV-Transparent Passive Concentrator", http://www.epa.gov/ppcp/project/star-grant1.html, Retrieved Aug. 6, 2010, 2 Pages.
J.R. Lakowicz "Principles of Fluorescence Spectroscopy", ISBN No. 978-0-387-31278-1, p. 27-61. 2006.
Chen et al. "Light Source Compensation in Absorption and Transmission Spectral Measurements", Acton Research Corporation, p. 1-3, 1998.
McPherson "Additive or Subtractive Mode Double Monochromator", http://www.mcphersoninc.com/spectrometers/uvvisir/model275d.htm, 2006, p. 1-2.
International Preliminary Report on Patentability dated Sep. 10, 2013, for corresponding PCT Application PCT/US2012/027833 filed Mar. 6, 2012.
International Search Report for PCT/US2012/027833, dated May 30, 2012.
Extended European Search Report for European Patent Application No. 12754324.7 dated Aug. 21, 2014.
International Search Report and Written Opinion for International Application No. PCT/US2015/055726 dated Feb. 12, 2016.
International Preliminary Report on Patentability for International Application No. PCT/US2015/055726 dated May 2, 2017.
Search Report and Written Opinion for Singapore Patent Application No. 11201703259U dated Mar. 21, 2018.
Yappert, M.C. et al.; Design and Evaluation of a Dual Multichannel Detector Spectrometer for Simultaneous Molecular Absorption and Luminescence Measurements; Analytical Chemistry; Mar. 3, 1989; vol. 61, No. 6; pp. 593-600.

(56) References Cited

OTHER PUBLICATIONS

Liyang Yang et al.; Estimating the Concentration and Biodegradability of Organic Matter in 22 Wastewater Treatment Plants Using Fluorescence Excitation Emission Matrices and Parallel Factor Analysis; Sensors 2014; pp. 1771-1786.
Jin Hur et al.; Prediction of BOD, COD, and Total Nitrogen Concentrations in a Typical Urban River Using a Fluorescence Excitation-Emission Matrix with PARAFAC and UV Absorption Indices; Sensors; 2012; pp. 972-986.
Partial Supplementary European Search Report for European Patent Application No. 15854992.3 dated Mar. 1, 2018.
Guo W et al.; Characterization of Dissolved Organic Matter in Urban Sewage Using Excitation Emision Matrix Fluorescence Spectroscopy and Parallel Factor Analysis; Journal of Environmental Sciences; vol. 22, No. 11, 2010; pp. 1728-1734 (No month).
Ruixia R et al.; Use of Three-Dimensional Excitation and Emission Matrix Fluorescence Spectroscopy for Predicting the Disinfection By-Product Formation Potential of Reclaimed Water; Water Research; vol. 46, No. 17, Aug. 14, 2012; pp. 5765-5776.
Extended European Search Report for European Application No. 15854992.3 dated Oct. 29, 2018.

\* cited by examiner

DETERMINATION OF WATER TREATMENT PARAMETERS BASED ON ABSORBANCE AND FLUORESCENCE

TECHNICAL FIELD

The present disclosure relates to an instrument for indirect determination of parameters used by water treatment facilities such as biological oxygen demand (BOD), chemical oxygen demand (COD), total organic carbon (TOC), trihalomethane formation potential (THMFP), etc. based on components identified using absorbance and fluorescence spectral analysis.

BACKGROUND

Water treatment plants, including those that treat surface water sources must generally meet various government requirements with respect to both the effluent distributed from the plant as well as intermediate by-products that may be created during the treatment process. In the United States, water treatment plants are required by the Environmental Protection Agency (EPA) to reduce the total organic carbon (TOC) concentration using a process of coagulation prior to disinfection of the finished water with halogenated/chlorinated disinfectants.

While various tools or instruments for monitoring TOC have been developed, online monitoring of TOC alone does not provide necessary information on the aromatic properties of the sample that are needed to determine the effective coagulation and disinfection dosages needed to prevent formation of toxic disinfection by products (DBPs). The aromaticity is the primary characteristic of the TOC that determines the chemical reactivity with halogenated disinfectants that results in toxic, carcinogenic DBPs.

Current convention uses separate measurements of the absorbance at 254 nm (A254 nm) and TOC concentration with separate instruments/detectors for the purposes of evaluating the effectiveness of the coagulation using what is known as the specific UV absorbance calculation, SUVA=A254 (m−1)/TOC (mg/l). The TOC and SUVA techniques do not provide a reproducible evaluation for different water sources because the aromatic properties of the organic composition of the source water often varies for a particular source over time, as well as among different sources. Further, the SUVA parameter is often imprecise due to the lack of kinetic simultaneity of the parameters of the TOC meter and absorbance detectors, as well as inherent propagated noise/interferences of the separate detection methods as conventionally implemented. Both TOC and A254 are prone to interferences of several types. Use of independent fluorescence data provides a means of ameliorating the influence of primary interferences.

While previous regulations for water treatment plants in the United States required averaged readings of disinfection byproduct formation levels of an entire distribution system, more recent EPA regulations require monitoring of local averages of disinfection byproduct formation levels in different regions of the distribution system. Monitoring only system wide averages may not be sufficient to detect local regions with higher propensity to form DBPs, which may be in violation of the more recent regulations outlined in the EPA Disinfection Byproduct Rule 2 (DBPR2). This of course heightens the need for more precise and accurate TOC and aromaticity evaluations for local regions of the treatment processes.

The imprecision of A254, TOC and SUVA as calculated using EPA specified methods (such as EPA Method 415.3) may also be attributed to the fact that both detector readings are aggregate, single point readings and therefore lack qualitative information on the effects of the coagulation treatment with respect to reactive organic species. As previously described, a number of interferences or confounding factors must be considered with respect to their effect on the readings, including inorganic carbon, metals like iron, and unknown contaminants that may or may not fluoresce. In addition, online TOC meters are highly prone to falling out of calibration, as are online DBP meters (gas chromatographs). Most water treatment plants cannot afford to install and maintain these pieces of equipment. However, as a result of the recent regulatory requirements, many water treatment plants in the United States are considering major infrastructure changes (tens of millions of dollars) including addition of ozone-destruction and ion exchange processes, such as the MIEX resin treatment process, for example.

Commercially available fluorescence instruments have been developed to facilitate parallel fluorescence and absorbance readings. Similarly, laboratory quality instruments are now commercially available to provide nearly simultaneous collection of absorbance and emission data for fluorescence reabsorbance correction. To provide the accuracy and flexibility for a wide variety of applications, these instruments may incorporate separate detectors for absorbance and fluorescence measurements with associated complex optical paths that incorporate a number of mirrors, beam splitters, lenses, and similar optical components, which results in a sophisticated instrument having an associated cost. In addition, the more complex optical arrangement may not be suitable for applications where frequent disassembly and cleaning of elements is required.

SUMMARY

A system configured to measure absorbance and fluorescence of a sample includes an input light source configured to generate at least one excitation wavelength, a chamber positioned to receive the sample and to be illuminated by the at least one excitation wavelength from the input light source, a detector positioned to selectively receive and detect light transmitted through the sample during an absorbance measurement, and emitted by the sample along a non-parallel excitation optical path during a fluorescence measurement in response to illumination by each of the at least one excitation wavelength, and an optical fiber positioned to receive light transmitted through the sample and direct the transmitted light to the detector during the absorbance measurement, wherein the light emitted by the sample during the fluorescence measurement is directed to the detector without passing through any optical fiber.

In one embodiment, a water treatment monitoring system configured to receive an on-line water sample associated with a water treatment process includes an input light source configured to generate at least one excitation wavelength, a reference detector positioned to receive a portion of the at least one excitation wavelength and generate a corresponding reference signal, a sample cuvette positioned to receive the on-line water sample and to be illuminated by the at least one excitation wavelength from the input light source, a multi-channel detector positioned to selectively receive and detect multiple wavelengths of light transmitted through the sample during an absorbance measurement, and emitted by the sample along an optical path generally perpendicular to an excitation optical path during a fluorescence measurement in response to illumination by each of the at least one excitation wavelength, an optical fiber positioned to receive light transmitted through the on-line water sample and direct the transmitted light to the multi-channel detector during the absorbance measurement, and a computer in communication with the reference detector and the multi-channel detector configured to correct the fluorescence and absorbance measurements based on the reference signal, correct the fluorescence measurement using the absorbance measurement, and determine a water treatment parameter based on the fluorescence and absorbance measurements of the on-line water sample.

In various embodiments, the water treatment monitoring system may include an order sorting filter positioned upstream of the multi-channel detector. The input light source may generate light having a nominal wavelength of 254 nm. The water treatment monitoring system may include a broadband light source with a narrowband filter passing light having a nominal wavelength of 254 nm. In some embodiments the water treatment monitoring system includes an input light source having a plurality of monochromatic light sources each having different output wavelengths and an optical fiber associated with each of the plurality of light sources to selectively couple one of the plurality of light sources to an output of the input light source. The output of the input light source may comprise an optical fiber. The reference detector may be coupled to the output of the input light source by an optical fiber.

The water treatment monitoring system may include a computer configured to take a first peak emission wavelength measurement of the in-line water sample and at least a second peak emission wavelength measurement of the in-line water sample emitted in response to the at least one excitation wavelength and to calculate the water treatment parameter based on a ratio of the second peak emission wavelength measurement to the first peak emission wavelength measurement. The sample cuvette may be implemented by a flow through cuvette with the on-line water sample flowing through the sample cuvette during the fluorescence and absorbance measurements. Alternatively, or in combination, the system may include at least one computer controlled valve to selectively stop flow through the sample cuvette during the fluorescence and absorbance measurements.

Embodiments according to the disclosure may also include a water treatment monitoring system configured to receive an on-line water sample associated with a water treatment process that includes plumbing configured to deliver pre-process and post-process water samples. A plurality of input light sources may each be configured to generate at least one excitation wavelength and have optical fibers associated with each of the plurality of input light sources. A light mixing pipe may be coupled to the optical fibers and configured to transmit the at least one excitation wavelength from a selected one of the plurality of fibers. The system may include a reference detector coupled to the light mixing pipe to receive a portion of the at least one excitation wavelength and generate a corresponding reference signal. A sample cuvette may be positioned to selectively receive the pre-process and post-process water samples and to be illuminated by the at least one excitation wavelength from the selected one of the plurality of input light sources. A multi-channel detector may be positioned to selectively receive and detect multiple wavelengths of light transmitted through the sample during an absorbance measurement, and emitted by the sample during a fluorescence measurement in response to illumination by each of the at least one excitation wavelength. The system may include a computer in communication with the reference detector and the multi-channel detector configured to correct the fluorescence and absorbance measurements based on the reference signal, correct the fluorescence measurement using the absorbance measurement, and determine a water treatment parameter associated with the water treatment process based on the fluorescence and absorbance measurements of the pre-process and post-process water samples.

Systems and methods according to various embodiments of the present disclosure may provide a number of advantages. For example, embodiments may be used to provide a more precise and accurate indirect determination of one or more water treatment parameters used for monitoring or control of water treatment facilities such as biological oxygen demand (BOD), chemical oxygen demand (COD), total organic carbon (TOC), and trihalomethane formation potential (THMFP) using online absorbance corrected fluorescence excitation-emission spectroscopy. Systems having a single multi-channel detector for fluorescence and absorbance measurements eliminate a potential source of noise and drift and are generally less expensive to manufacture so that multiple systems may be used to monitor water treatment processes at a water treatment plant. Use of optical fibers to couple the relatively stronger absorbance signal to the multi-channel CCD detector while using a more direct optical path for the relatively weaker fluorescence signal facilitates use of a single detector while also accommodating insertion of a calibrated light source via the optical fiber for wavelength and spectral accuracy calibration of the CCD detector. Fewer optical elements facilitates disassembly for cleaning and reassembly to accommodate higher frequency sampling facilitated by on-line acquisition of water samples and processing times on the order of seconds to minutes.

Various embodiments provide simultaneous determination of the TOC, aromaticity and SUVA parameters using one or more online instruments positioned at one or more key points of a water treatment system. A synchronized calibrated network of online instruments provides full ultraviolet-visible (UV-VIS) absorbance and corrected fluorescence emission spectra on the order of milliseconds to seconds for real-time or near real-time monitoring and control of one or more treatment processes. Embodiments of the system and method of this disclosure facilitate cost-effective improvement of current water treatment infrastructure methodology (such as using enhanced coagulation or additional granular activated carbon) to ameliorate predicted disinfectant byproduct (DPB) spikes as well as to avoid overdosing of coagulant when DBP potential is low.

The online absorbance and fluorescence spectral analyses according to embodiments of this disclosure may be used to identify or flag unknown contaminations as new components. The system or method for indirect determination of a water treatment parameter according to embodiments of this disclosure include a model that uses the spectral analyses to determine various application or process specific treatment parameters to monitor and/or control the treatment process. The system and method of various embodiments may be used to detect membrane fouling agents for a variety of membrane systems including: reverse osmosis, microfiltration, ultrafiltration and membrane bioreactors and forward osmosis (ceramic membranes). Fouling agents may have associated spectral peaks. As such, the system and method may be used for a variety of treatment plants including desalination, wastewater recycling and industrial treatment as well as for shipboard ballast purification systems using membrane technology. The model may be tuned for various applications including surface water treatment, wastewater treatment, or industrial treatment processes. In various embodiments, the model is tuned to protein like peaks for sewage treatment to provide an indirect determination of biologic oxygen demand (BOD) or chemical oxygen demand (COD). Similarly, the model may be tuned to oil peaks for an oil recycling application, etc. Oxygen concentration is another factor that can be quantified in the model as an influencer of the quantum yield of the component species for ozone treatment monitoring.

Other applications and advantages of a system or method according to embodiments of the present disclosure include use to effectively monitor and accurately determine the replacement period for bio-active carbon (BAC) filters by analyzing the levels or ratios of C1-C4 components. The BAC activity primarily influences the protein-like peaks following ozone treatment. This can potentially save millions of pounds of activated carbon and millions of dollar a year. One water treatment facility has estimated that it can extend the useful life of their BAC filter mats for up to several years at huge cost savings with an accurate measurement of effectiveness rather than following the recommendation for annual replacements by the carbon mat suppliers.

Using instruments with one or more multichannel detector(s), collection and processing of the absorbance and fluorescence data is effectively instantaneous (within seconds) relative to many offline analysis strategies. Based on the representative embodiments disclosed, algorithms can be easily calibrated and validated to precisely and accurately quantify the compounds removed specifically by coagulation, ozone, or other processes.

The online absorbance and fluorescence measurements may be combined with other online monitor quality metrics including nephelometric turbidity units (NTU), chlorine dose and residual, pH, alkalinity (hardness), and temperature, for example, can easily be incorporated into a continuously updated predictive model for highly effective determinations of disinfection byproduct formation potential and TOC.

The above advantages and other advantages and features of the present disclosure will be readily apparent from the following detailed description of the preferred embodiments when taken in connection with the accompanying drawings.

DETAILED DESCRIPTION

Various representative embodiments of systems and methods according to the present disclosure are described in detail. However, it is to be understood that the representative embodiments are merely exemplary and systems and methods according to the present disclosure may be embodied in various and alternative forms. The figures are not necessarily to scale and some features may be exaggerated or minimized to show details of particular components. Therefore, specific structural and functional details disclosed herein are not to be interpreted as limiting, but merely as a representative basis for teaching one of ordinary skill in the art to variously employ the present invention. Simplified flowcharts or block diagrams may be provided to illustrate operation of a representative embodiment of a system or method. Those of ordinary skill in the art will appreciate that the order of steps or processes may not be required for particular applications, that some steps may have been omitted for ease of illustration and description, and that steps or processes may be repeated individually and/or as a subset of the illustrated steps or processes. Likewise, all illustrated or described steps may not be needed to provide one or more the advantages described herein.

As those of ordinary skill in the art will also understand, various features of the present disclosure as illustrated and described with reference to any one of the Figures may be combined with features illustrated in one or more other Figures to produce embodiments of the present disclosure that are not explicitly illustrated or described. The combinations of features illustrated provide representative embodiments for typical applications. However, various combinations and modifications of the features consistent with the teachings of the present disclosure may be desired for particular applications or implementations.

Figure 1:
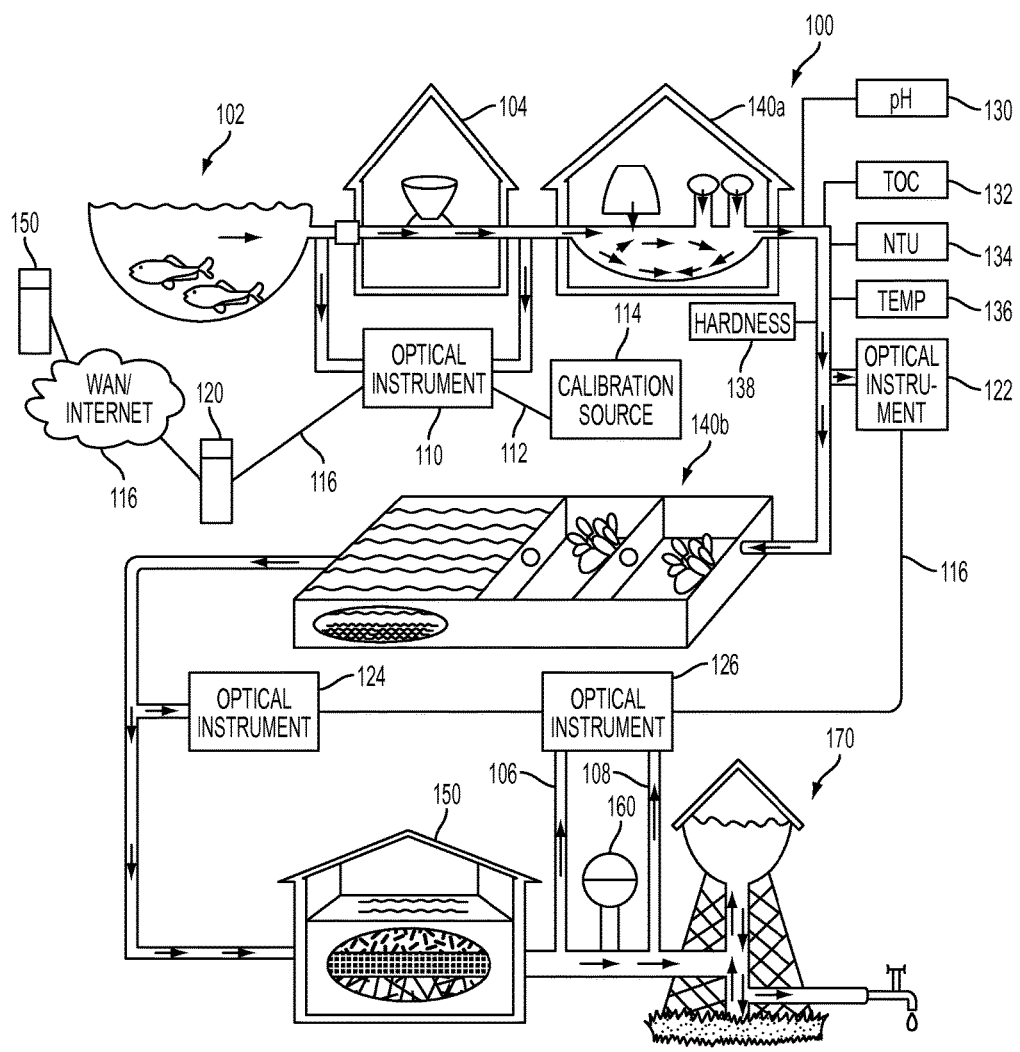
FIG. 1 is a simplified block diagram illustrating a representative water treatment facility for treating surface water and positioning of instruments for monitoring and/or controlling one or more treatment processes using water treatment parameters determined according to the present disclosure.

A simplified block diagram illustrating a representative water treatment facility having various water treatment processes is shown in FIG. 1. While various embodiments are illustrated and described with respect to a representative water treatment process used for surface water treatment, various embodiments may include other types of water treatment facilities and/or processes. As described in greater detail below, concepts described in the present disclosure may be applied to a wide variety of treatment processes to monitor and/or control the process. Online monitoring using absorbance and fluorescence measurements according to embodiments of the present disclosure may be used to improve the precision and accuracy of a number of parameters used to monitor or control various water treatment processes, including but not limited to BOD, COD, DOC, TOC, THMFP and various other parameters.

While a number of variations exist, most surface water treatment facilities have a number of key processes that include dilution, coagulation/flocculation, settling, filtration, and disinfection. Various other chemical treatments or processes may also be used depending on the type of source water and expected contaminants. The complexity and type of treatments or processes may depend on the quality of the source water and variation over time based on the effectiveness of source-water protection and management programs.

As illustrated in FIG. 1, a representative surface water treatment facility 100 may receive surface water from one or more sources, such as a river, lake, reservoir, etc. as generally represented at 102. Water treatment facility 100 may include one or more holding areas, tanks, or reservoirs 104 to provide dilution or mixing of sources. An optical instrument 110 may be positioned online at the inlet from one or more sources, and/or after combination of source water. Online instrument 110 facilitates real-time monitoring of one or more water treatment parameters that may be directly or indirectly determined based on absorbance and fluorescence measurements for use in monitoring or controlling subsequent treatment processes. Online instrument 110 may communicate over a wired or wireless network 116 with a local monitoring or control computer/server 120 as well as one or more remote computers/servers 150 that may communicate over a wide area network (WAN) such as the internet or cloud. In addition, online instrument 110 may be optically coupled via one or more optical fibers or cables 112 to a calibration source 114 for in-situ calibration as described in greater detail below. Similarly, online instrument 110 may communicate directly or indirectly over a wired or wireless network with other similar instruments 122, 124, 126 that provide absorbance and fluorescence measurements, as well as sensors or meters such as pH sensor 130, TOC meter 132, turbidity detector 134, temperature sensor 136, and hardness sensor 138. Those of ordinary skill in the art will recognize that the types, numbers, and locations of instruments, sensors, detectors, meters, etc. may vary by particular application and implementation.

Depending on the particular application and implementation, a single (or common) instrument may be used to measure or monitor a water treatment parameter before and after a particular treatment process rather than having separate instruments, as represented by optical instruments 110, and 126. Plumbing 106, 108 may be provided to route online samples from upstream and downstream of one or more treatment processes to a single/common instrument. While this may provide cost savings by reducing the number of instruments needed for monitoring of the desired treatment processes, the cost savings may be reduced by additional water sample routing and control to a common location, as well the additional manual or automatic hardware required to change the sample flow through the instrument. Instruments or monitors may be positioned at key locations relating to essential steps in the treatment plant as previously described. These usually include at least the inlet, after coagulation-settling, and at the plant effluent. Online monitors positioned at these locations, or one or more central or common monitors that receive online samples from these locations, may be used to sample the water flow at regular time intervals. Water treatment parameters and associated measurement or determination protocols may be developed for particular types of treatment facilities. Representative water treatment parameters and associated representative measurement methods or protocols according to embodiments of the present disclosure are described below.

Water treatment facility 100 may include a flocculation and/or coagulation process as generally represented at 140a and 140b, respectively. As known, coagulation/flocculation may include addition and mixing of chemical coagulants or filter aids that cause small suspended particles to stick together to form larger particles that more readily settle out or can be more easily filtered. The type and quantity of coagulants may depend on the microbial and chemical components of the water. This process in combination with a settling process may be used to remove organic carbon materials from the water to reduce formation of undesirable disinfection byproducts during the subsequent disinfection treatment/process 160. The coagulation process may be monitored and/or controlled by comparing measurements from instrument 124 positioned downstream or subsequent to coagulation process 140 with one or more upstream instruments, such as instruments 110, 122 as described in greater detail herein.

A settling or sedimentation process (not shown) may follow coagulation/flocculation process 140a-b, particularly in applications treating water that contains significant solids. The settling or sedimentation process slows the flow of the water in a basin or pond to allow heavier items to settle to the bottom rather than being carried in the flow to the next process. Online instrument 124 may be positioned downstream of such a sedimentation process with measurements used to determine one or more water treatment parameters used to monitor or control the process by comparing measurements with an upstream instrument, such as instrument 122 or 110, for example. A settling or pre-sedimentation process (not shown) may be used prior to the dilution process 104 in some applications.

After settling or sedimentation, a single or multi-step filtration process 150 may employ a variety of methods to filter particles from the water. The type of filtration may vary based on the raw water quality. As filtration implies, water flows through a material that captures and removes particles, organisms, and/or contaminants. Granular media such as sand, crushed anthracite coal, or granular activated carbon (GAC) are often used as filter media. Different types and sizes of media may be layered and may operate at different flow rates. Membrane filtration may also be used in some applications, but may not be well-suited for highly contaminated source waters because of membrane clogging. Membrane filtration is gaining use in the United States for special applications and in combination with other types of filtration. Online instrument 126 may be positioned downstream of filtration process 150 with associated measurements used to determine water treatment parameters for monitoring or controlling the process. In the representative embodiment illustrated, online optical instrument 126 may receive water samples after filtration process 150, as well as samples after disinfection process 160.

While filtration and the steps prior to filtration focus on the physical removal of contaminants in the water, disinfection is used to kill or inactivate bacteria and viruses that may pass through the physical removal steps. Viruses and organisms like giardia are effectively killed by chlorine. Some organisms, such as *Cryptosporidium* may be resistant to chlorine, but are susceptible to treatment by ozone and ultraviolet light. In some countries, ozone and UV light may be used without chlorination to kill bacteria and other organisms. In the representative application for an optical instrument and associated monitoring and control of a water treatment facility, disinfection process 160 provides chemical disinfection, but may also generate undesirable disinfection byproducts when reacting with organic carbon components. Disinfectants may include chlorine, chloramines (chlorine plus ammonia), ozone, ultraviolet light, and chlorine dioxide, for example. The advantage of chlorination is that it continues to kill bacteria as water moves through the distribution system 170. Its disadvantage is the possibility of potentially harmful disinfection byproducts. Excess chlorine in water can combine with organic material in the water to form substances such as trihalomethanes, which have been linked to various adverse human health effects over a lifetime exposure. Use of one or more online instruments to monitor and/or control one or more water treatment processes or parameters according to embodiments of the present disclosure may reduce disinfection byproducts by more accurate monitoring and control of one or more upstream processes, such as coagulation process 140b, in addition to more accurate monitoring and control of the disinfection process 160.

Various other treatment processes, may be used to treat or condition the water at various points of the overall treatment process. For example, chemicals may be added to drinking water to adjust its hardness (softness), pH, and alkalinity to reduce corrosion in the distribution system 170, which may include pipelines, storage tanks, and building plumbing systems, for example. Similarly, fluoride may be added to the water to enhance dental health.

Figure 2A:
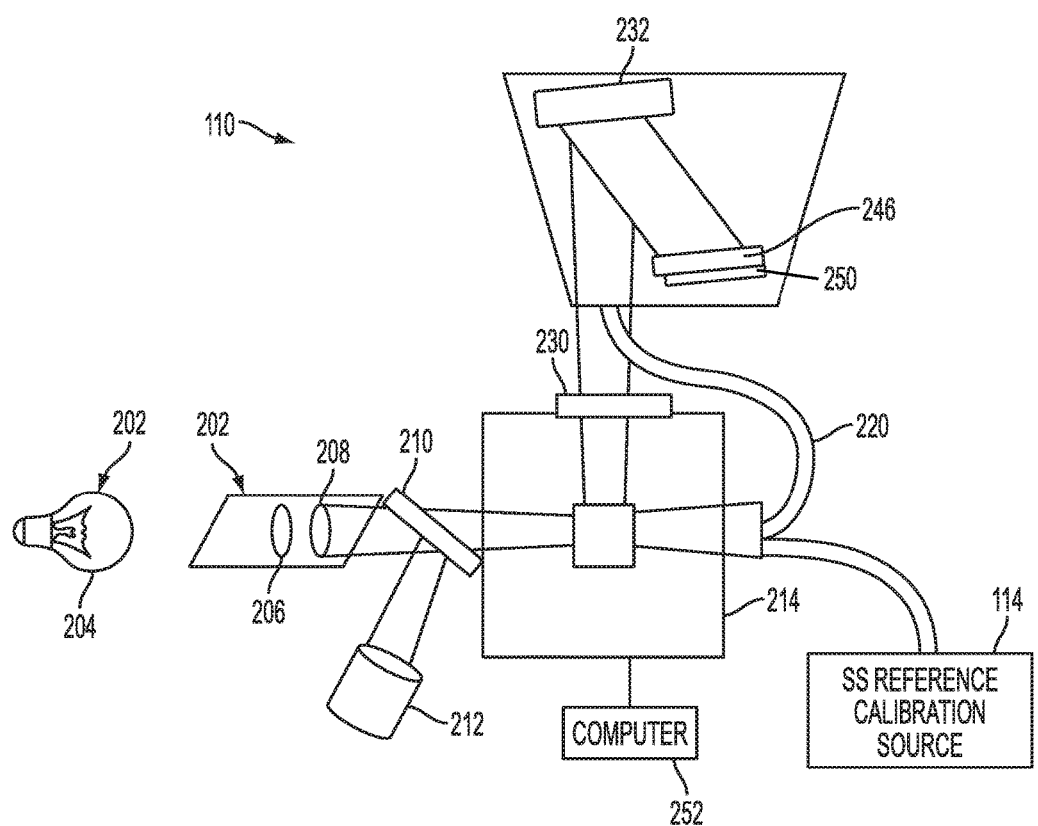
FIG. 2A is a simplified block diagram of an instrument that may be used to provide absorbance measurements and absorbance corrected fluorescence excitation-emission spectra measurements for use in indirect determination of water treatment parameters according to embodiments of the present disclosure.

FIG. 2A is a simplified block diagram of an instrument that may be used in a system for monitoring a water treatment process to provide absorbance measurements and absorbance corrected fluorescence excitation-emission spectra measurements for use in indirect determination of water treatment parameters according to embodiments of the present disclosure. Other instruments may be used to provide similar absorbance and absorbance corrected fluorescence measurements according to the present disclosure, such as those disclosed in copending and commonly owned U.S. patent application Ser. No. 13/042,920, the disclosure of which is hereby incorporated by reference in its entirety. A commercially available implementation of such an instrument is the AQUALOG™ available in the United States from Horiba Scientific division of Horiba Instruments Incorporated of Edison, N.J. While suitable for a variety of applications, the AQUALOG™ may be more costly than various embodiments disclosed herein as it was designed for a wider variety of applications and includes a double subtractive monochromator for the input light source as well as separate detectors for obtaining the absorbance and fluorescence measurements.

As generally illustrated in FIG. 2A, a representative instrument, such as instrument 110 includes an excitation light source 202 that may include a narrow or broadband light source 204 used in combination with one or more filters, such as white light filter 206 and excitation filter 208. Alternatively, a white light filter 206 may be replaced with a white light diode used in combination with excitation filter 208. In other embodiments, an excitation diode emitting light of the desired excitation wavelength(s) may be used in place of a light source in combination with an excitation filter. As described in greater detail below, excitation filter 208 (or an excitation diode or source) is selected to provide narrowband light having a wavelength of 254 nm with a bandwidth of about 2 nm. Light from source 202 passes through a beamsplitter 210 with a portion reflected to a reference detector 212 to provide light and temperature compensation. Use of a reference diode or detector 212 for excitation monitoring and correction provides traceable optical correction of fluorescence excitation spectra and compensates for any input lamp drift. However, the reference diode 212 is not required and various embodiments do not include such a reference diode or detector.

Light transmitted through beamsplitter 210 passes through a sample chamber implemented by a flow-through cuvette 214 in this embodiment and having a fixed path length and positioned using quartz rods/guides (not shown). Water from one or more treatment processes or steps as described above with reference to FIG. 1 is routed to flow-through cuvette 214 for analysis.

Light passing through cuvette 214 may be coupled to fiber link 220 and routed to multi-channel detector 250, implemented by a CCD device in various embodiments. Fiber link 220 includes a linear array of fibers to route the light transmitted through cuvette 214 to grating 232 and a separate portion of detector 250 so that a single CCD or other multichannel detector 250 may be used for both absorbance and fluorescence measurements to reduce instrument cost. This is particularly beneficial in reducing system costs associated with incorporating a network of instruments/monitors to monitor or control multiple steps or processes within a water treatment facility according to embodiments of the present disclosure. In addition, use of a fiber coupling or link 220 facilitates insertion of light injected from a solid state reference material and/or a calibrated light source 114 for wavelength and spectral accuracy in calibration of multichannel detector 250. This facilitates in-situ calibration of the instrument which may provide various advantages in applications such as a water treatment facility that may employ multiple instruments at various locations to monitor particular treatment processes or sequences as described in greater detail herein.

Light generated by fluorescence of the sample within flow-through cuvette 214 passes through an emission filter 230 to grating 232, which separates the light into wavelength bands before passing through order sorting emission filter 246 to multi-channel detector 250. Similarly, as previously described, light passing through cuvette 214 travels through fiber coupling link 220 and is routed to grating 232 and to detector 250 for obtaining absorbance measurements. Instrument 110 includes a computer 252 to receive the absorbance and fluorescence measurements and correct the fluorescence spectrum using the absorbance measurements. The measurements may be communicated over a local or wide area network 116 to a separate computer/server 120, 150 for use in determining various water treatment parameters and for monitoring and controlling the water treatment process. Alternatively, the computer associated with any particular instrument may be used to determine the water treatment parameters and communicate them to a central monitoring/control computer, server, or system. The computer associated with each instrument may also perform various instrument control functions such as control of sample water routed to cuvette 214, control of one or more shutters (as shown in FIG. 2C) positioned to block light from light source 202, or in the absorbance or fluorescence optical paths for use during calibration etc. The computer may also correct measurements using the reference detector 212.

Other embodiments of the instrument may include use of separate multichannel detector-spectrographs to measure fluorescence and absorbance. However, use of an instrument having a single multichannel detector-spectrograph to substantially simultaneously measure fluorescence and absorbance may provide various advantages. The main advantage of such an instrument is the full spectral correction afforded by the multichannel detectors along with rapid data collection and processing. In other embodiments where these considerations are less important, the detector may be implemented by a single channel detector, such as a PIN photodiode.

Figure 2B:
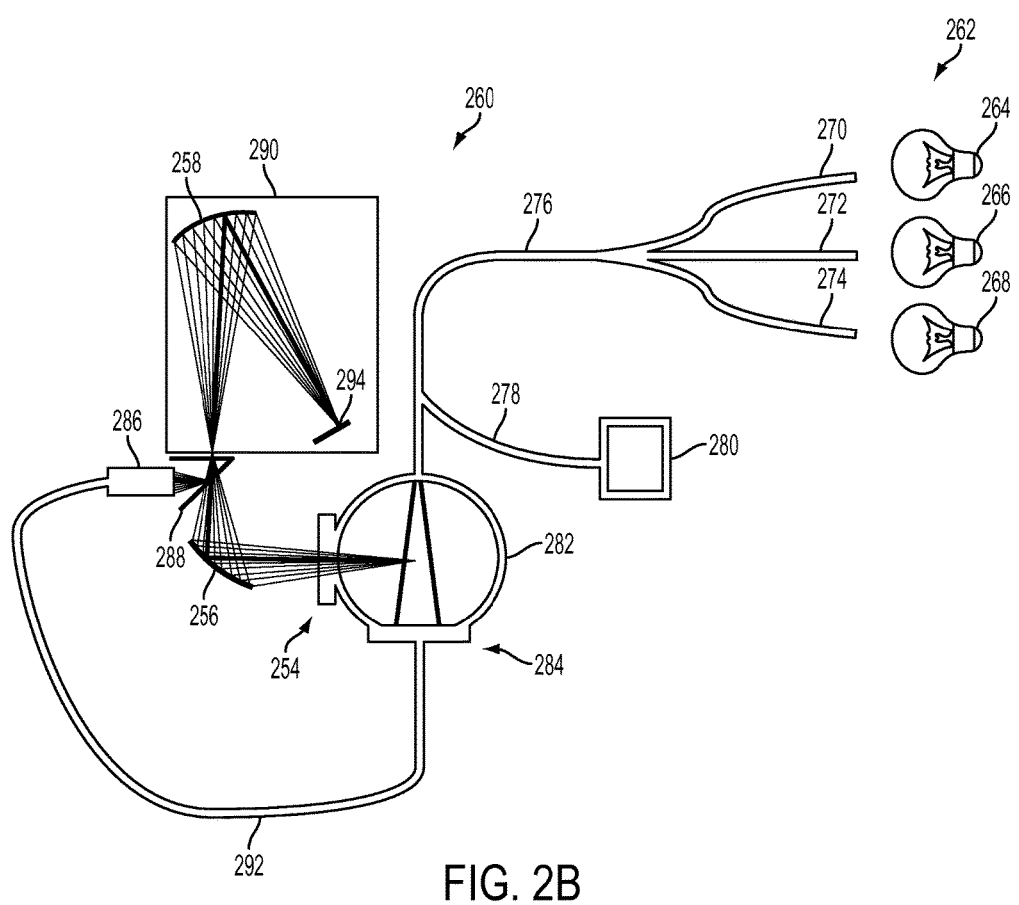
FIG. 2B is a simplified block diagram of an alternative embodiment of a system for monitoring a water treatment process having multiple input light sources coupled via optical fibers.
Figure 2C:
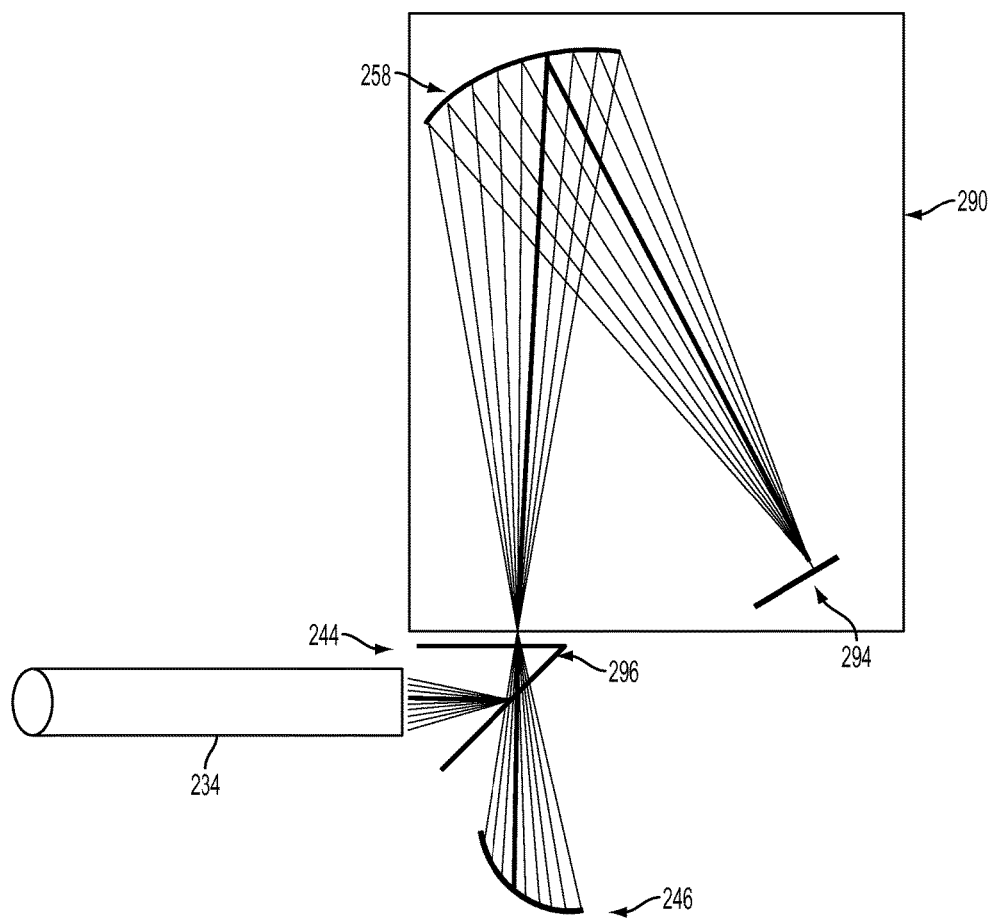
FIG. 2C is a simplified block diagram of an alternative embodiment of components of a detector or spectrograph for use in a system for monitoring a water treatment process.

FIG. 2B is a simplified block diagram illustrating another embodiment of a system for monitoring a water treatment process. System 260 includes an input light source 262 comprising a plurality of separate monochromatic and/or broadband light sources including a monochromatic light source 264 emitting monochromatic light at a frequency of 254 nm, a broadband light source 266 emitting white light used during calibration, and a monochromatic light source 268 emitting light having an application specific wavelength, for example. Light sources 264, 266, and 268 are coupled to associated optical fibers 270, 272, and 274, respectively. A light mixing pipe 276 may be used to deliver light from a selected input source for use in calibration or measurements by CCD spectrograph 290. Use of fiber optics and control electronics (not specifically illustrated) to control the input sources may be used to provide for shutterless operation and operates to selectively couple one of the plurality of light sources 264, 266, 268 to an output of the input light source 262.

As also shown in the embodiment of FIG. 2B, an optional reference diode detector 280 is coupled to the light mixing pipe 276 by an optical fiber 278. When present, reference diode detector 280 provides an associated reference signal that may be used by the system computer to correct the absorbance and fluorescence measurements for variations in the input light characteristics. Light mixing pipe 276 is coupled by optical components to sample chamber 282. Plumbing may be configured to provide on-line or flow through operation to deliver water samples to sample chamber or flow-through cuvette 282 for absorbance and fluorescence measurements. One or more computer controlled valves (FIG. 1) may be used to control the flow to sample chamber 282. The sample chamber, flow cell, or flow-through cuvette 282 is illustrated in cross-section looking top to bottom with flow of sampled water from top to bottom with the option of solenoid valves to periodically stop flow coordinated with triggering of the sampling process. Pre-process (treatment) and post-process samples may be routed to the same instrument as previously described. Alternatively, different instruments may be used to analyze pre-process and post-process samples with results communicated over a network and compared to monitor and/or control the associated treatment process. In one embodiment, flow of sampled water through cuvette or sample chamber 282 is stopped during absorbance and fluorescence measurements. Other embodiments may include a flow-through cuvette 282 with sample water flowing through cuvette 282 during the measurements.

In the embodiment of FIG. 2B, CCD spectrograph 290 is positioned to receive excitation light from input source 262 passing through cuvette 282 and shutter 284 into optical fiber 292 after being focused by optics 286 and reflected by beam combiner 288. Optical fiber 292 is provided to couple light from the transmission path to the multi-channel CCD 294 for the absorbance measurements similar to the representative embodiment illustrated in FIG. 2A. In other embodiments, multi-channel detector 294 may be replaced by a single channel detector, such as a photodiode, for example.

As also shown in FIG. 2B, fluorescence light emitted by sampled water within sample chamber 282 may be emitted along a non-parallel path or at a generally perpendicular angle relative to the absorbance light transmitted through sample chamber 282 and shutter 284 to fiber 292. The fluorescence light passes through an associated shutter 254 and is reflected by a focusing mirror 256 through beam combiner 288 and into entrance slit of spectrograph 290, where it is reflected by grating 258 onto detector 294.

FIG. 2C is a block diagram illustrating an optical fiber coupling for a spectrograph in a system for monitoring a water treatment process according to embodiments of the present disclosure. Spectrograph 290 includes a beam splitter/combiner 296 that reflects a significant portion (96% in one embodiment) of incident fluorescence light from fiber 234, which is coupled to the sample cuvette or chamber (not shown), to grating 258 and a CCD detector 294 with an order sorting filter (not shown). Beam splitter/combiner 296 combines a small portion (4% in one embodiment) of the relatively stronger incident absorbance light reflected from mirror 246 through entrance slit 244 to grating 258 and detector 294.

As illustrated in FIGS. 2A-2C, various embodiments employ an optical fiber to deliver the relatively higher intensity light passing through the sample during the absorbance measurement to the detector, while using various optics without passing through any optical fiber to deliver the lower intensity light emitted by the sample during the fluorescence measurement to the detector. While the representative embodiments illustrated may use one or more fibers to deliver the excitation light to the sample, or the absorbance light to the spectrograph, other embodiments may use discrete optical components to provide a suitable optical path from the excitation light source to the sample and/or from the sample to the spectrograph.

Figure 3A:
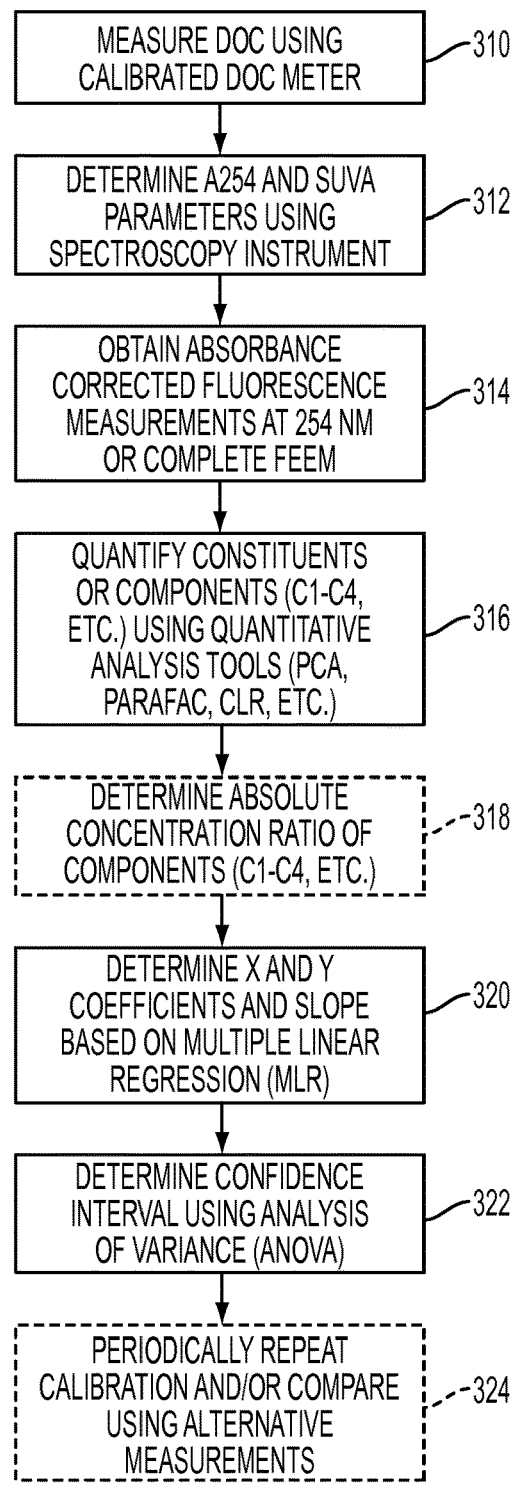
FIGS. 3A and 3B are simplified flow charts illustrating calibration and operation of a system or method for indirect determination of water treatment parameters according to embodiments of the present disclosure.
Figure 3B:
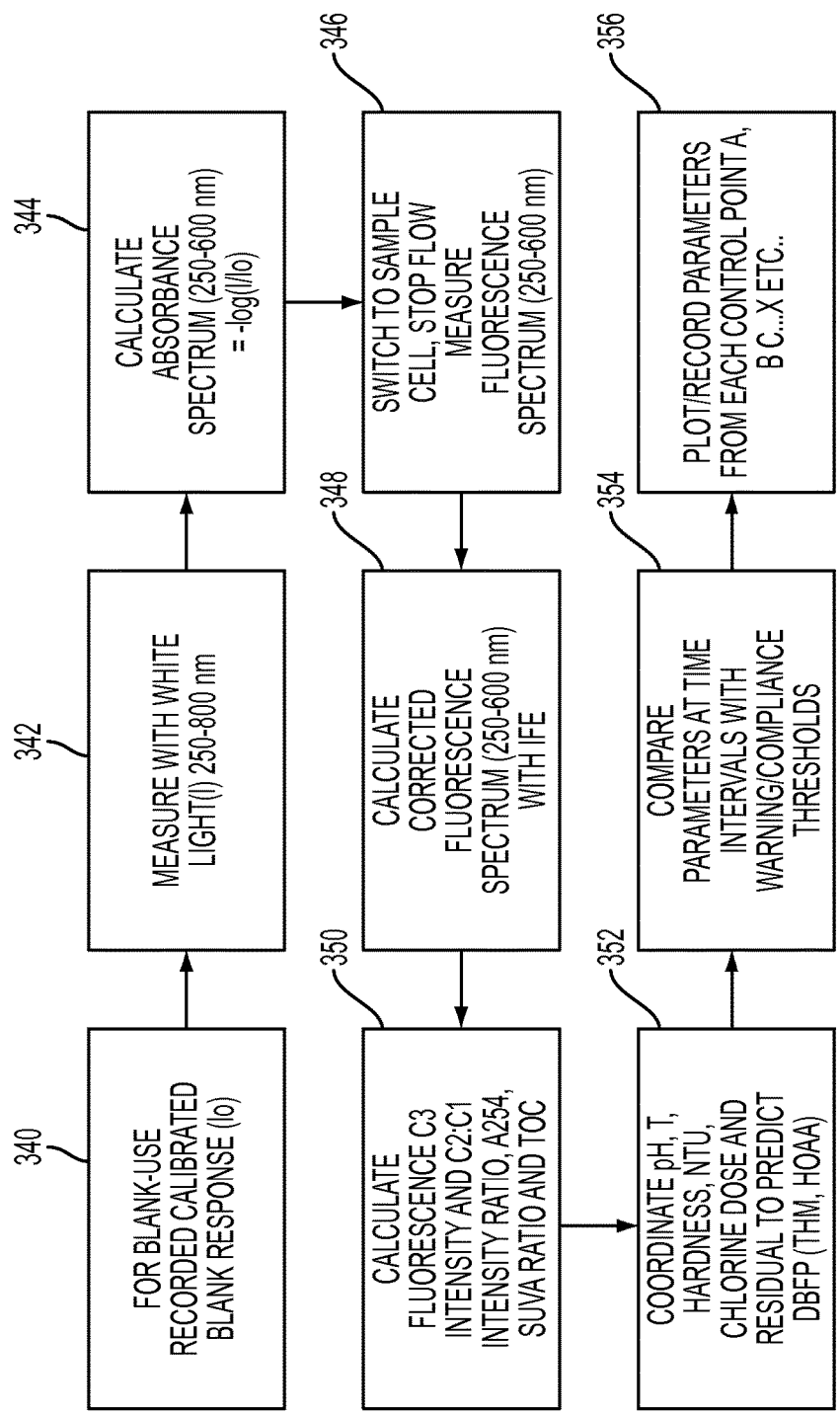

FIGS. 3A and 3B are simplified flow charts illustrating calibration and operation of a system or method for indirect determination of water treatment parameters according to embodiments of the present disclosure. As represented by the flow charts in FIGS. 3A and 3B, a water treatment parameter such as total organic carbon (TOC) or dissolved organic carbon (DOC) is determined or evaluated from absorbance and fluorescence spectral data using one or more online detectors 110, 122, 124, 126 alone or in combination with sensors and meters such as one or more pH sensors 130, TOC meters 132, turbidity detectors 134, temperature sensors 136, and hardness sensors 138 that communicate within a detector network. Each online optical detector 110, 122, 124, and 126 may be synchronized with the other online optical detectors. TOC (or DOC) meter readings and other parameters are correlated with treatment steps or processes periodically as per regulations to verify online sensors and optical instruments.

Optical instruments/detectors 110, 122, 124, 126 are positioned at select treatment steps to monitor complete absorbance spectrum and inner-filter effect corrected fluorescence emission spectra at selected excitation wavelengths including but not limited to 254 nm (A254) for total and aromatic carbon concentration, key chlorophyll wavelengths, key petroleum or contaminant wavelengths, protein peaks for BOD/COD etc. Regular recording of DOC can be used to calibrate optical online meters as a function of treatment steps and account for quality differences within and between treatment facilities or plants.

In the representative embodiments of FIGS. 3A and 3B, the absorbance and fluorescence measurements obtained from the optical instruments 110, 122, 124, and 126 are used to determine water treatment parameters, such as dissolved organic carbon (DOC) or total organic carbon (TOC), for example, as described below.

The absorbance at 254 nm (represented by A254 nm) corresponds to:

A254 nm=$\varepsilon_{254\ nm}$.DOC.1, where $\varepsilon_{254\ nm}$ is the molar extinction coefficient, DOC is the dissolved organic carbon concentration usually expressed in (mg/l) and 1 is the absorbance path length. DOC generally comprises a sum of 3 to 4 well defined spectral components (C1-C4) or species that are of natural origin with different fluorescence emissions when excited at 254 nm including:

C1=High molecular weight humic/fulvic acids (excitation (ex) 254 nm, emission (em) 475 nm);

C2=Mid to low molecular weight (MW) humic and fulvic acids (ex 254 nm, em 425 nm);

C3=protein like components (ex 254 nm, em 350 nm); and

C4=low mw and protein like components (ex 254 nm, em 325 nm)

Virtually all naturally sourced surface water can be modeled as a sum of components C1 to C3 accounting for >99% of spectral variance. It follows then that the fluorescence spectrum excited at 254 nm contains >99% of the information needed to evaluate changes in any of the 3 or 4 components as a function of a particular water treatment process or sequence of processes.

Various process parameters such as C1, C2, A254, pH, temperature, etc. may be selected to indirectly determine the desired monitoring parameter, such as DOC, TOC, THMFP, etc. Selection of suitable parameters may include identifying the parameters such as C1, C2 pH temperature, etc. having some relationship or correlation with the monitoring parameter(s). Once these parameters are identified, a linear combination of the parameters may be determined. For example, a linear combination such as xA254+yC1/C2+zpH+ . . . . The relationship between measured values and the linear product is used to determine the slope and x, y, and z scaling factors using any of a number of curve fitting strategies, such as multiple linear regression (MLR), for example. This process is repeated over time with measurements from representative samples for the particular application to fine tune the slope, scaling factor(s), and/or base parameters used in the linear combination to achieve a desired correlation between the base parameter and the monitoring parameter.

In one embodiment for monitoring a water treatment process, TOC was selected as the monitoring parameter. To select the base parameters and determine the slope and scaling factors for the linear combination used to indirectly determine TOC, the component concentrations or values for C1 and C2 were selected that correlate with the SUVA value because the .SUVA correlates with the aromatic DOC component. The .A254/DOC values correlate with the aromatic component concentration of C1 and C2. The C1 component is the humic component with the highest aromaticity and molecular weight (MW) and the strongest correlation with high SUVA aromaticity index. The C2 component is the fulvic/humic component with lower MW and aromaticity and hence correlates with a low SUVA aromaticity index. C3 and other components with deeper UV absorbance and emission than C1 and C2 are generally less influenced by, and therefore not well correlated with coagulation. They are much lower in aromaticity and tend to vary independently of coagulation as compared to C1 and C2 so they are not effective predictors of aromaticity. As such, C3 and C4 were not selected because including these components in an MLR prediction of TOC or DOC would result in poor correlation and predictive capability of the selected process monitoring parameter.

The integral of the DOC fluorescence spectrum measured from 290-600 nm in response to excitation at 254 nm is represented by:

$$\int_{290\ nm}^{600\ nm} F_\lambda = \int_{290\ nm}^{600\ nm} C1 + \int_{290\ nm}^{600\ nm} C2 + \int_{290\ nm}^{600\ nm} C3 + \int_{290\ nm}^{600\ nm} C4$$

The quantum contribution of each component (C1-C4) excited at 254 nm is defined in general as:

$$\Phi C_x = A254 C_x \cdot T \cdot pH$$

Where temperature (T) and (pH) may influence quantum contributions but generally the contributions statistically are negligibly different among the four components and pH also plays a minor role across treatment process for the four components, meaning temperature and pH are normally not large factors in typical surface water treatment applications, but are accounted for in the model to provide broader applicability.

Water treatment directly alters the apparent molar extinction coefficient (254 nm) primarily by changing the relative concentrations of the components (Cx), as opposed to changing their quantum yields or generating new fluorescent components. As such, evaluating the (normalized) spectral profile of the fluorescence spectrum excited at 254 nm provides a direct measurement of the relative concentrations of the components C1-C4. The normalized spectral profiles captured from samples taken before and after a particular treatment process or series of treatment processes may be used to monitor and/or control the process(es) as described in this disclosure. Evaluation of the spectral profiles may be performed using various techniques as generally represented and described with reference to FIGS. 5-8.

The largest influence of coagulation (as a representative treatment example) is to reduce the apparent molar extinction coefficient ($\varepsilon_{254\ nm}$) by reducing the concentration of C1 relative to the total or sum of components of $C_{tot}$=(C1+C2+C3), which provides a direct measurement of the aromatic concentration. The ratio of C1:$C_{tot}$ is linearly related to, and the primary cause of the change in slope of A254/DOC, which is also referred to as the specific UV absorbance (SUVA). In many applications, various treatment processes may not affect all of the components C1-C4 equally. As such, the particular ratio used to monitor or control a particular process may vary. For example, the concentrations of C3 and C4 are not significantly changed by a coagulation treatment process. As such, the process can be monitored, evaluated, and/or controlled by determining corresponding treatment parameters, such as DOC, using a ratio of C1:C2 rather than C1:$C_{tot}$.

As one can see from the above description, C1:$C_{tot}$=xSUVA where x is a simple linear scaling factor such that the relationship remains linear for:

$$DOC = A254\ nm/\varepsilon_{254\ nm} \cdot 1$$

because changes in the molar extinction coefficient ($\varepsilon_{254\ nm}$) are linearly related to the sum of the components represented by $C_{tot.}$ in this example.

As previously described, C4 is not normally detected as a natural component in surface water treatment. However, it may be monitored for detection of particular types of pollutants and is highly prevalent in sewage sourced wastewater and water sources receiving treated sewage. The changes in components represented by C1-C4 can be monitored continuously and evaluated by comparing spectra from the different detectors 110, 122, 124, 126, etc. in the network within a particular treatment facility 100, or among treatment facilities. Representative comparisons are illustrated and described with respect to FIGS. 5-8.

The optical signal processing of the present disclosure is designed to monitor two main sources of relative and absolute component variation of the DOC. For natural and manmade raw source variation, the relative DOC component contribution varies depending on several factors of the source water including rain and storm events, fire events, leaf fall events, algal blooms, sewage discharge, etc. For treatment process variation, the primary effect of the coagulation and filtration processes is to influence the total DOC as well as the relative aromatic carbon component ratios. The main function of the treatments is to reduce the probability of the formation of regulated and undesirable halogenated disinfection byproducts by reducing the precursor components contained within the DOC.

The flowcharts of FIGS. 3A and 3B provide a representative experiment or measurement protocol or method including instrument calibration that may be used at a monitoring or control point for a particular water treatment process. The water treatment parameters indirectly determined, calculated, or measured may vary depending on the particular treatment process being monitored or controlled.

FIG. 3A is a flow chart illustrating a representative calibration process for use in indirect determination of water treatment parameters according to embodiments of the present disclosure. A calibrated DOC meter is used to measure DOC as represented at 310. A commercially available DOC meter may be used with the DOC meter calibration procedure specified by the manufacturer and/or a calibration process approved by a regulatory agency or standards organization, for example. An instrument such as described and illustrated with reference to FIG. 2 is then used to determine A254 and SUVA parameters as represented by block 312. In various embodiments, A254 and SUVA parameters are determined according to U.S. EPA Method 415.3 for an initial calibration period (e.g. 30-90 days) of normal water treatment (or other facility) plant operation for raw, settled, and effluent sample sets.

With continuing reference to FIG. 3A, the instrument is used to measure or obtain an absorbance corrected fluorescence spectrum (ranging from 290 nm to at least about 600 nm, for example) in response to excitation at 254 nm as represented at 314. Alternatively, a complete fluorescence excitation emission spectrum (FEEM) may be obtained for each corresponding DOC and A254 reading from block 310. Constituents or components within the samples are then quantified using one or more quantitative analysis tools as represented by block 316. Quantitative analysis tools may include principal component analysis (PCA), parallel factor analysis (PARAFAC, which is a generalization of PCA), classical linear regression (CLR), peak value analysis, etc. to identify or quantify each of a plurality of components within the samples. This step may include quantification of various components associated with the particular process being monitored or controlled. Various embodiments according to the present disclosure quantify components C1-C4 as previously described for use in monitoring and/or control of a water treatment process.

Alternatively, or in combination, an absolute concentration ratio of components may be determined as represented by block 318. In one embodiment, an absolute concentration ratio of C1:C2 is determined along with the corresponding A254 measurement for use as linear coefficients (x and y) with the intercept fixed at 0 mg/l to predict DOC. According to embodiments of the present disclosure, predicted DOC may be represented by a generally linear function (x[C1]: [C2]+yA254) as described in greater detail with reference to FIGS. 4-8.

A multiple linear regression (MLR) is used to determine the x and y coefficients and corresponding slope as represented by block 320 and as described in greater detail with reference to FIG. 4. The predictive MLR model determined at block 320 is evaluated to determine a correlation coefficient using analysis of variance (ANOVA) to determine a confidence interval for the slope as represented at 322.

The calibration may be periodically checked as generally represented by block 324 although this is not part of the calibration process per se, but is provided for purposes of illustration of a representative water treatment process. In particular, the predictive MLR model may be applied in continuous sampling mode with periodic re-evaluation compared to daily batch analyses, for example. The C1:C2 ratio may also be determined as a surrogate of the Aromatic Index and compared to SUVA.

As illustrated in the flowchart of FIG. 3B, in one embodiment, the fluorescence emission spectrum (250 nm to 600 nm, for example) is measured with a CCD-spectrograph, such as instrument 110, in response to an excitation filtered to 254 nm. The instrument may be calibrated with a blank with data stored in a non-transitory computer readable storage medium for future use as represented by $l_o$ at block 340. An absorbance measurement is performed with the white light (1) source (from 250 nm to 800 nm, for example) using an order sorted photodiode array spectrograph as represented at 342. The absorbance spectrum is calculated for 250 nm to 600 nm as $-\log(l/lo)$ as represented at 344. The instrument is then used to determine the fluorescence spectrum of a sample cell as represented at 346. In one embodiment, the sample flow through the flow-through cuvette is stopped during the absorbance and fluorescence measurements. However, in other embodiments the sample water may continue to flow during the measurements, although this may introduce additional variation in the results.

The absorbance spectral data (250 nm to 600 nm=$-\log(l/l_o)$) is used to calculate a corrected fluorescence spectrum to adjust for primary and secondary inner filter effects (IFE) as represented at 348. The fluorescence emission spectrum excited at 254 nm provides quantitative information on the TOC fractions (C3, C4) associated with proteins (aromatic amino acids), but more importantly (for the representative embodiment illustrated) the lower molecular weight and aromaticity (C2) and the higher molecular weight and aromaticity humic and fulvic acid components (C1) associated with the SUVA parameter. The selected water treatment parameters, SUVA and TOC in this example, are then calculated or determined based on the fluorescence intensity C3, fluorescence intensity ratio C2:C1 and the absorbance A254 as represented at 350. The TOC can be determined based on the absorbance and fluorescence data using the predetermined relationship between the measured TOC using a TOC meter and the predicted TOC, which may be represented as the linear combination of the absorbance and fluorescence as illustrated and described in greater detail herein, for example.

Other water treatment parameters may also be determined or calculated using the absorbance and fluorescence measurements. In the representative embodiments illustrated in FIGS. 3A and 3B, measurements of pH, temperature (T), and chlorine dose and residual are used to predict or determine water treatment parameters associated with disinfectant byproduct formation potential (DBFP), such as trihalomethanes (THM) and haloacetic acids (HAA), for example, as represented at 352. One or more water treatment parameters may be compared with an associated warning/compliance threshold at designated or periodic time intervals as represented by 354. A calibrated or numerical model may be used to evaluate changes in concentrations of one or more components, such as concentrations of C3, C4 associated with protein emission (330 and 350 nm); concentration C2 of low molecular weight humic/fulvic components (420 nm); and concentration C1 of higher molecular weight humic/fulvic components (450-475 nm). The water treatment parameter(s) may be recorded and/or plotted for each control point or treatment process as represented at 356.

FIGS. 4-8 illustrate examples of determining component concentrations and/or ratios for use in a system or method for determining a water treatment parameter according to embodiments of the present disclosure. The representative embodiment illustrated determines component concentrations for C1 and C2 as previously described. However, determination of additional component concentrations or alternative component concentrations and/or ratios may be performed depending on the particular application and implementation. Absorbance spectra in response to an excitation source having a nominal wavelength of 254 nm is collected from an online instrument for samples taken before and after a representative treatment process or series of treatment processes as represented at 410. The A254 value represented at 416 is subsequently used in combination with the component values or ratios (C2:C1 in this example) to indirectly determine a predicted water treatment parameter, such as TOC, as represented at 418. In the embodiment illustrated, the absorbance spectrum is plotted as a function of wavelength for a sample taken before a treatment process (coagulation in this example) as represented by data 412 and for a sample taken after a treatment process as represented by data 414. As such, data 412 represents the absorbance of a raw water sample and data 414 represents a water sample after treatment. The absorbance data is used for inner filter effects (IFE) correction as represented at 420 of the fluorescence spectra data represented by the plots 430, which show normalized intensity as a function of corrected emission wavelength in response to the excitation nominal wavelength of 254 nm. Depending on the particular application and implementation, IFE may not be required to provide acceptable results. The fluorescence spectra represented at 430 include pre-treatment (raw) model data 432, post-treatment model data 434, pre-treatment (raw) measured data 436 and post-treatment data 438. The sample data was fit to a validated three-component (C1-C3) parallel factor analysis model with a high degree of correlation as described in greater detail herein.

The fluorescence spectra data 430 can be analyzed using various quantitative analysis strategies as generally represented by blocks 440, 442, 444, and 446 and illustrated and described in greater detail with reference to FIGS. 5-8 to determine the changes in the aromatic component intensities (such as C1 and C2, for example) and ratios (C1:C2 or C2:C1, etc.). The component concentrations or ratios from these analyses as represented at 450 are combined with the A254 nm readings represented at 416 to calculate the TOC using multiple linear regression (MLR) as represented at 418. As illustrated by the plot 418 with the predicted data as a function of the measured data, the predicted or modeled data exhibits a generally linear relationship with the measured or directly determined data as previously described. A multiple linear regression (MLR) 460 was used to determine x and y coefficients as previously described with respect to FIGS. 3A and 3B to model the treatment parameter as a linear combination of the A254 absorbance data represented at 416 and the fluorescence data represented by 450 corresponding to the ratio or component concentrations of C1 and C2 expressed as C2:C1, or alternatively $C_{tot}$:C1 for total organic concentration (TOC) in this example. In various embodiments the component concentrations are used instead of a ratio of component concentrations. Similarly, calculation of a component concentration may not be required. Rather parameters that correlate with the component concentrations may be used, such as peak height as described in greater detail herein.

As demonstrated by the strong positive correlation illustrated in data 418, the absorbance and fluorescence data can be used to indirectly determine a water treatment parameter, such as TOC, using a corresponding model without the need for a corresponding TOC meter. This provides various advantages with respect to the ability to accurately monitor the treatment process with an online instrument as previously described. In particular, use of the absorbance and fluorescence data provide a reproducible evaluation for different water sources that may have variable aromatic properties over time or between sources. The kinetic simultaneity of the absorbance and fluorescence measurements provide a more precise determination of SUVA that eliminates propagated noise and interferences of the separate detection methods that rely on a TOC meter as conventionally implemented. The more precise and accurate TOC and aromaticity evaluations afforded according to embodiments of the present disclosure facilitate compliance with more stringent regulations for water treatment plants.

Figure 4:
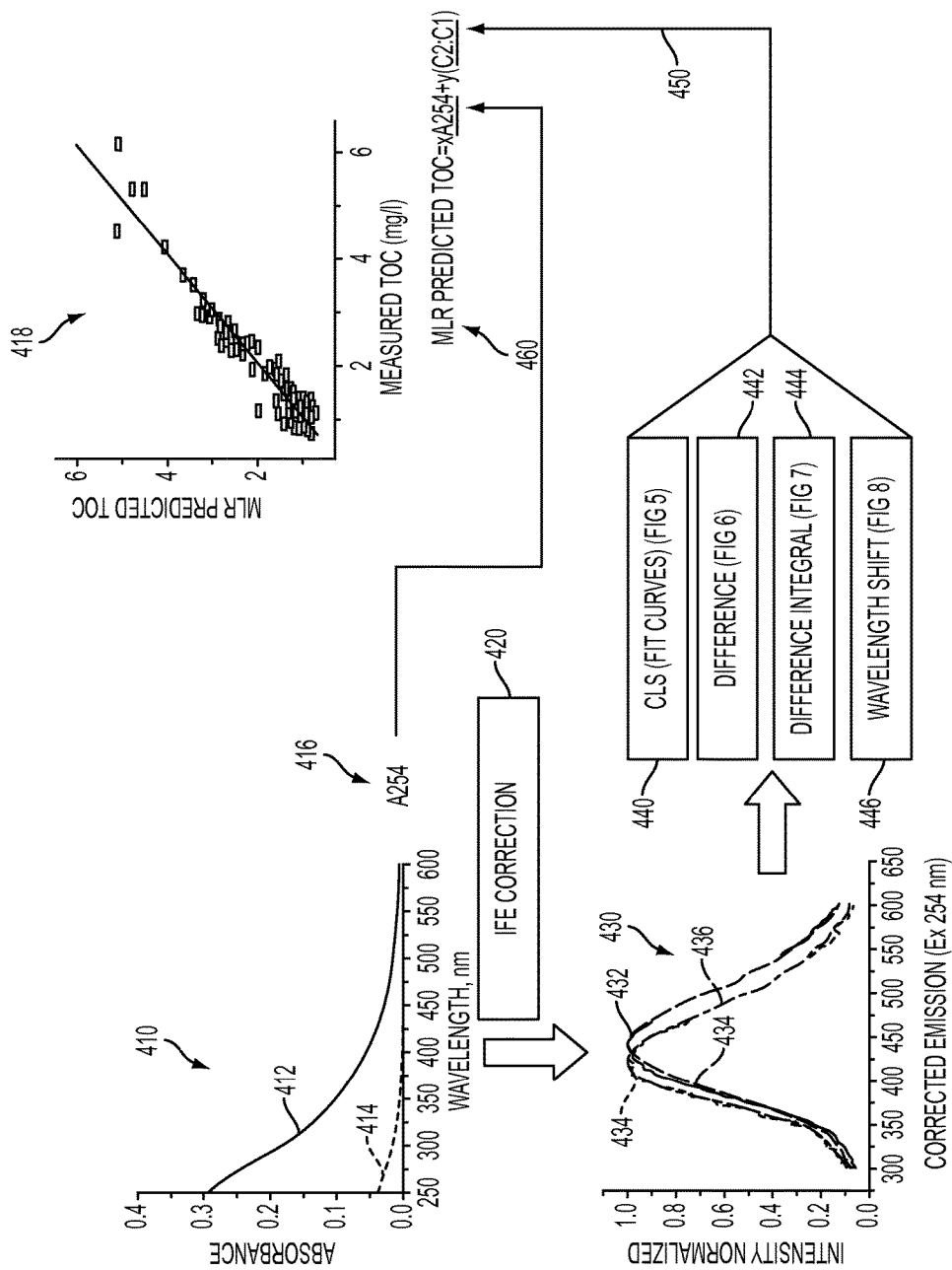
FIGS. 4-8 illustrate examples of determining component concentrations C1 and C2 or similar components for use in indirect determination of a water treatment parameter according to embodiments of the present disclosure.

While the representative embodiment illustrated in FIG. 4 was used to demonstrate the ability to indirectly determine TOC, other water treatment parameters may be determined in a similar manner, such as SUVA, THMFP, etc.

As previously described, the changes in C1-C4 or other components being monitored in particular applications can be monitored continuously and evaluated by comparing absorbance and corrected fluorescence spectra from different detectors positioned to analyze samples from desired points within a particular treatment process or series of processes. Various numerical operations may be employed for quantitatively evaluating the spectral shape change associated with the change in concentration ratios from a particular source or as a result of a particular treatment process or series of processes.

As illustrated and described with reference to FIG. 4, the fluorescence spectra can be analyzed as represented by blocks 440, 442, 444, and 446 as illustrated and described in greater detail with reference to FIGS. 5-8 to determine the changes in the aromatic component intensities and/or associated ratios. In the representative embodiments illustrated, the component ratios from these analyses are combined with the A254 nm readings to calculate the TOC using multiple linear egression (MLR).

Figure 5:
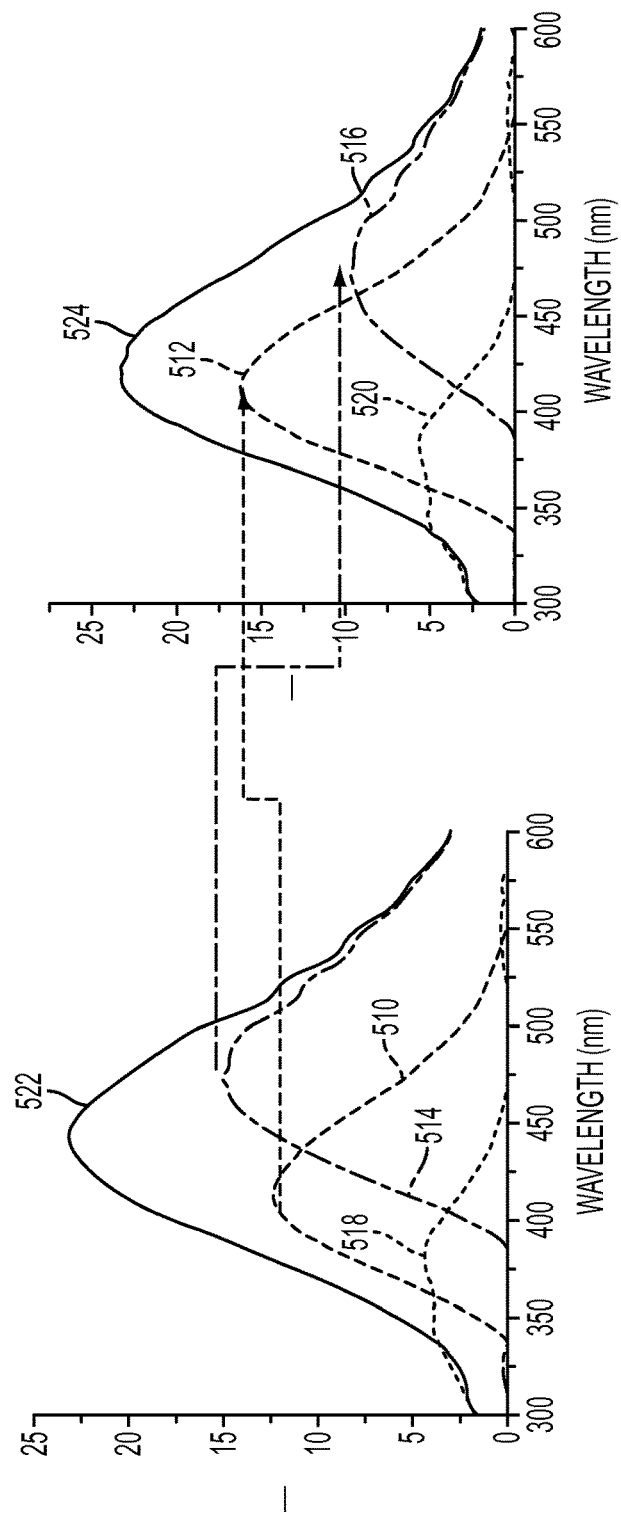

FIG. 5 shows a classical least squares fit (CLS) for data associated with the main components C1, C2, and C3 for the raw and treated samples to indicate the relative changes in the aromatic components C1 and C2. Intensity data is plotted as a function of wavelength from 300 nm to 600 nm. Data 510 represents C1 in raw samples before a representative treatment process, while data 512 represents effluent samples after treatment. Similarly, data 514 represents intensity for component C2 in raw samples while data 516 represents intensity values for component C2 in effluent samples. Data 518 represents intensity values for component C3 while data 520 represents intensity values for C3 in effluent samples. Data 522 represents intensity values for the sum of components C1, C2, and C3 in raw samples, while data 524 represents intensity values for the component sum in effluent samples.

Figure 6:
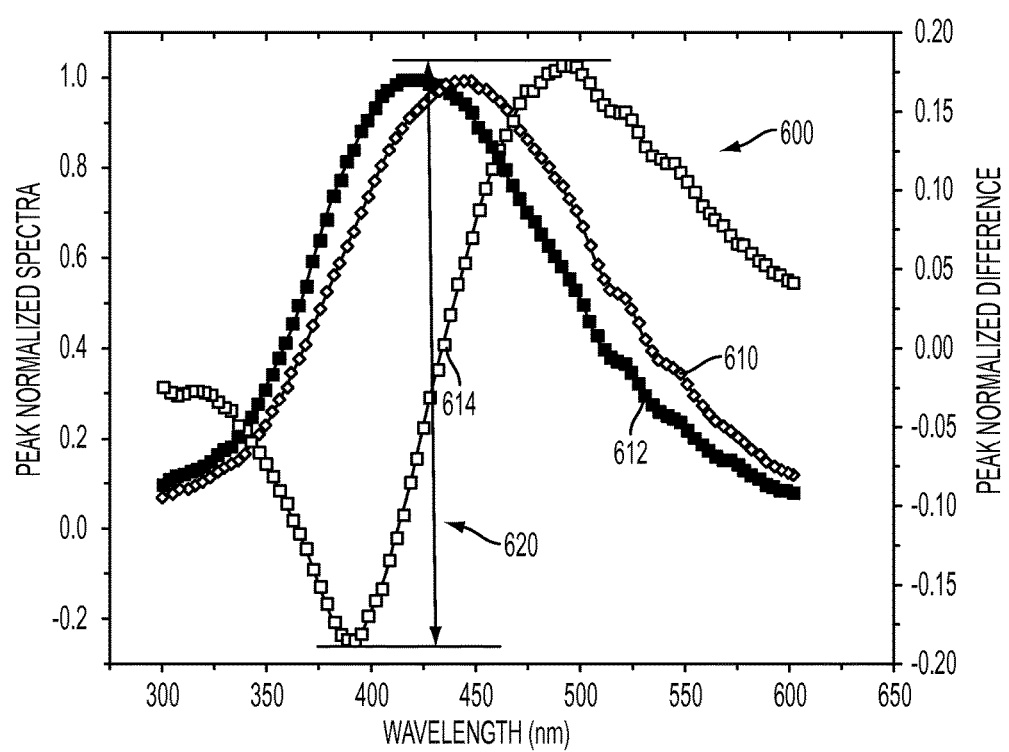
Figure 7:
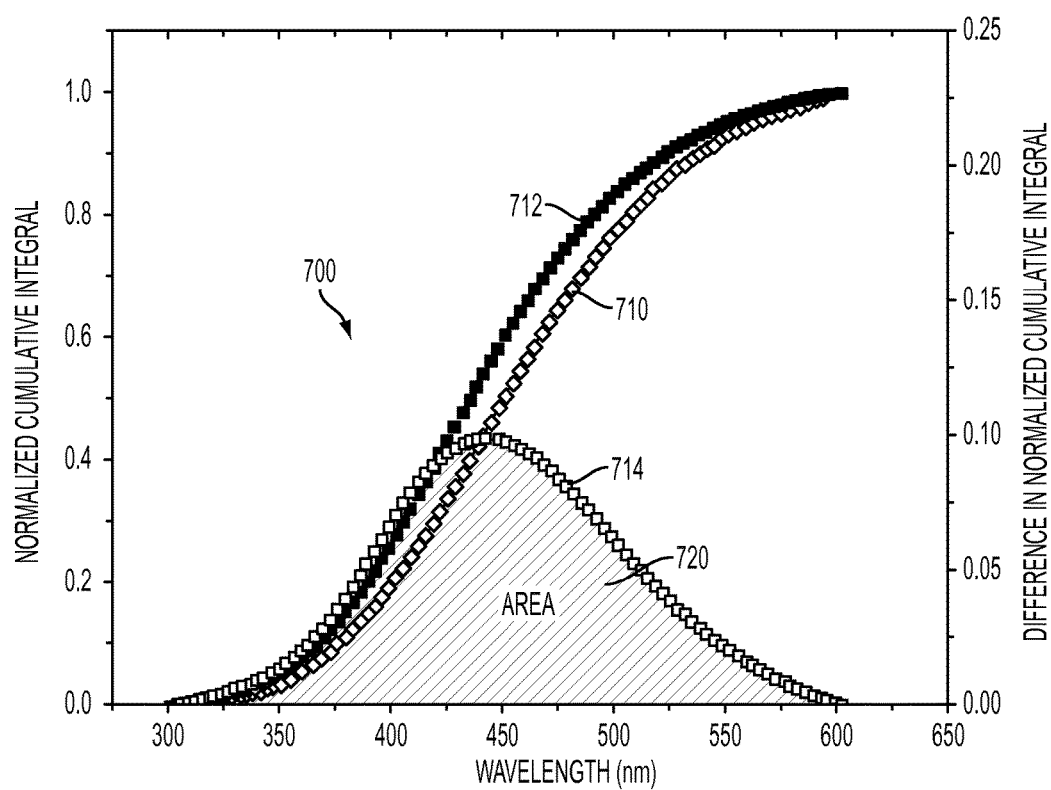
Figure 8:
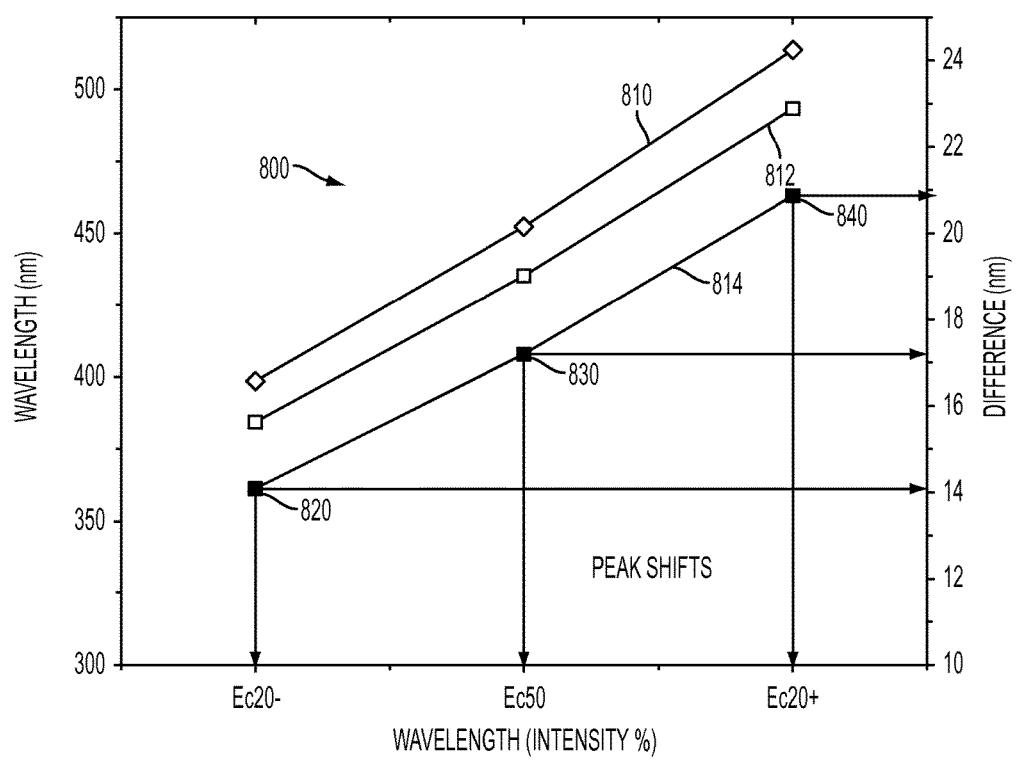

FIGS. 6-8 illustrate numerical approaches that will provide quantitative information independent of the need to perform least squares curve fitting. FIG. 6 shows how the normalized spectra can be used to calculate the difference in the raw and treated spectra to measure the changes in the spectral intensities proportional to the C1 and C2 concentration changes. Data 600 includes data representing pre-process or raw peak normalized absorbance corrected fluorescence spectrum data 610, post-process or effluent peak normalized absorbance corrected fluorescence spectrum data 612, and the difference data 614. As illustrated in FIG. 6, the change or shift in the spectral center of gravity from pre-treatment to post-treatment data leads to negative values in the difference spectra. This results from the peak wavelength center shift associated with removal of C1 components during the coagulation treatment process. The magnitude or change in the peak difference data is represented at 620.

FIG. 7 illustrates use of normalized integrals of raw and treated sample spectra to calculate the difference or change in area proportional to the change in the C1 and C2 components. Data 700 includes the normalized cumulative integral data for a pre-treatment or raw sample 710, a post-treatment or effluent sample 712, and the difference spectrum data 714. The area 720 corresponds to the integral of the difference data 714 over the associated wavelength range. Normalization of the cumulative integral of the spectrum at each treatment step as a function of wavelength may be the most effective measure for confirming the quantitative change evaluated as the difference of the normalized integral spectra between steps. As illustrated in FIG. 7, the signal area 720 of the difference spectrum remains positive and linear with the component ratio change resulting from the coagulation treatment process. Similar results may be obtained for other types of treatment processes using corresponding identification of related components and the effect of a particular treatment process or series of processes on a particular component concentration or ratio of component concentrations. As also illustrated by the data represented in FIG. 7, and illustrated and described in greater detail with reference to FIG. 8, the change or shift in wavelength coordinates or value associated with the peak of the difference data 714 may be quantitatively related to the component concentration changes and may be used to monitor and/or control a particular treatment process or series of treatment processes FIG. 8 shows how the wavelength coordinates at −20 nm from the peak, at the peak and +20 nm from the peak of each spectrum can be used to calculate the changes in the C1 and C2 component intensities. Line 810 represents pre-treatment or raw sample data Line 812 represents post-treatment or effluent sample data and line 814 represents the difference data or change between lines 810 and 812. As illustrated in FIG. 8, peak 820 shifts 14 nm from pre-treatment to post treatment. Peak 830 shifts about 17 nm, and peak 840 shifts about 21 nm from pre-treatment to post treatment.

As illustrated in FIGS. 4-8, the absorbance and fluorescence spectral analyses may be used to identify the presence of unknown contaminations as new components in the samples. As those of ordinary skill in the art will recognize, the same type of component model can be tuned to protein-like peaks for sewage treatment (BOD or COD), oil peaks for oil recycling etc. While other excitation wavelengths may be used for particular applications, the 254 nm is a very high signal peak in the excitation spectra of all natural DOC components. It should be recognized that oxygen concentration is another factor that can be quantified in the model as an influencer of the quantum yield of the components. As such, similar analyses may be used for ozone treatment monitoring and control.

Because the system and method rely primarily on the relative changes in the normalized fluorescence spectral shape, area, and maxima, the component concentration changes for the fluorescence spectra can also be calculated numerically based on ratiometric, subtractive, and/or derivative analyses to speed calculation rather than using a calibrated classical least squares (CLS) approach to fit the fluorescence data to the known component spectral shapes as previously described. In addition, absorbance and fluorescence ranges can be extended to include chlorophylls and accessory pigments from algae with appropriate excitation filters and gratings in the associated online instrument(s). In addition, the relationship between protein components (C3) can also be used to monitor biochemical and chemical oxygen demand parameters for waste-water treatment as previously described.

During development and model validation, samples were collected to compare the fluorescence and absorbance spectral data of raw source water from a canal and after coagulation/filtration treatment. The model used to treat the data was first validated using complete fluorescence excitation-emission matrices (EEMs) corrected for fluorescence inner filter effects and with parallel sample measurements of the total organic carbon measured independently with a TOC meter. The EEM data set originally comprised 204 samples and was fit to a validated three component parallel factor analysis model with a high degree of correlation (greater than 98%) and split half validated correlation (greater than 97.8%). The three components were clearly identified as a low molecular weight humic/fulvic component (C1), a high-molecular weight humic/fulvic component (C2), and protein components (C3). Analysis of samples taken after a coagulation/filtration treatment demonstrated that the treatment lowers the relative concentration of C2 compared to C1 with little if any effect on C3.

The SUVA data calculated from the A254 nm and TOC parameters was compared to the ratio of the C2:C1 components as a function of analysis date for samples collected over the course of several days to monitor the effect of sample variation. Comparison of the SUVA parameter to the C2:C1 ratio was used to demonstrate that changes in SUVA (measured using separate absorbance and TOC meter readings) may be more precisely measured using the C2:C1 ratio measured simultaneously with absorbance and corrected fluorescence instrument according to embodiments of the present disclosure. The SUVA calculations showed raw water was greater than 4 and settled and effluent samples were generally around 2-3 with significant (>19 to13%) scatter in the treated samples.

The C2:C1 ratio, which is a linear factor in relation to TOC, mirrored the SUVA trend with a lower coefficient of variance in the treated samples (<5 to 3%) for better resolution of aromaticity changes among the three treatments. Monitoring of the A254 and TOC meter data as a function of analysis date was performed to illustrate the consistency of the changes in the source water composition. The measured TOC and A254 values used for the SUVA calculations were used to demonstrate that treatment resulted in two linear relationships between the raw and treated water consistent with the SUVA and C2:C1 ratios. Based on this data, it is clear the changes in the linear relationships between the raw and treated data sets as a function of TOC is consistent with the systematic change in the molar extinction of the samples that is determined by the relative reduction in the C2:C1 component ratio according to Beer's Law.

As such, the present disclosure recognizes that knowing the C2:C1 ratio, concentrations, or other correlated values, and A254 value enables the calculation (by the process of multiple linear regression or similar methods) of the TOC for the data sets using one predictive equation. The multiple linear regression equation results indicate a high degree of precision and accuracy of the TOC ($R^2$>0.988). Therefore, knowing the fluorescence emission spectrum and absorbance spectrum allows simultaneously determination of the SUVA and TOC concentrations with one instrument that can operate online for TOC ranges from <<0.5 to >10 mg/l with high confidence. Online instruments according to the present disclosure can determine these and similar water treatment parameters or indicators within a matter of seconds for each sample using instruments having few moving parts.

Figure 9:
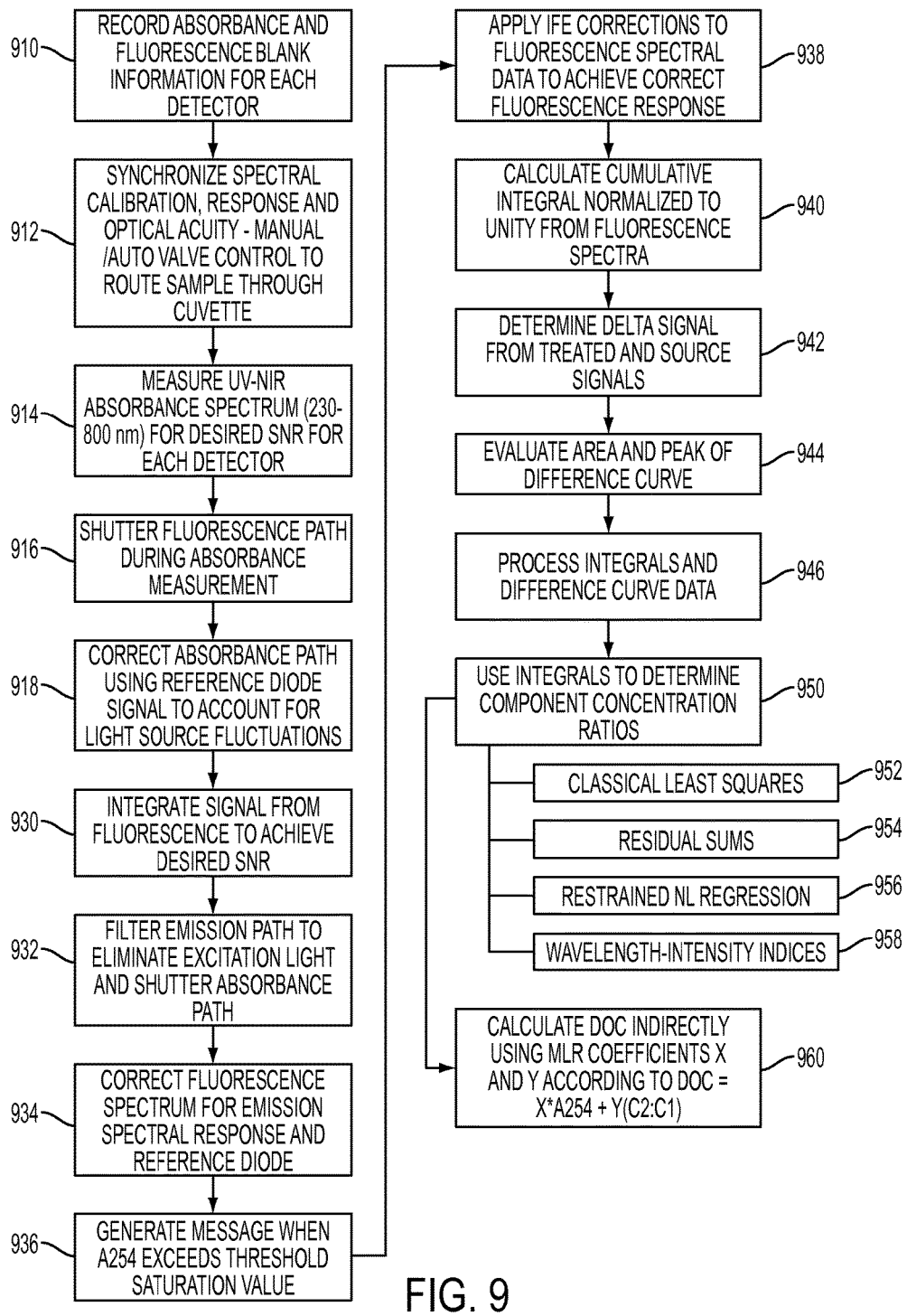
FIG. 9 is a flow chart illustrating operation of a system or method for determining a water treatment process parameter or indicator, such as dissolved organic carbon (DOC), total organic carbon (TOC), or trihalomethane formation potential (THMFP), for example, using absorbance and fluorescence measurements according to embodiments of the present disclosure.

FIG. 9 is a detailed flow chart illustrating a system or method for determining a water treatment process parameter, such as dissolved organic carbon (DOC), total organic carbon (TOC), or trihalomethane formation potential (THMFP), for example, using absorbance and fluorescence measurements according to embodiments of the present disclosure. The absorbance and fluorescence spectral blank information is recorded for each detector in the network as represented at 910 and each detector is synchronized for spectral calibration and response and optical acuity (cleanliness) as represented at 912. In various embodiments, the detector may be calibrated in situ using remote fiber access to the CCD spectrograph for calibration and reference material light sources and samples.

The sample flow can be temporarily halted with manually or automatically controlled valves to route a particular sample to the flow through cuvette as represented at 912 for subsequent absorbance and fluorescence determination to provide analysis synchronization as described below. The complete UV-NIR absorbance spectrum is measured from 230-800 nm using an order sorting filter equipped (OSF) CCD-spectrograph until a desired signal to noise is obtained for each detector location as indicated at 914. The fluorescence path is shuttered to prevent scattered light from entering this path to the CCD during absorbance measurement at 916. The absorbance path is corrected by the reference diode signal to account for light source fluctuations as represented at 918.

The sample's fluorescence emission spectrum is excited at 254 nm and the signal is integrated until the desired signal to noise is reached for each detector location as represented at 930. The emission path is filtered to eliminate any excitation light and the absorbance/transmittance path is shuttered to prevent illumination of the CCD through this path during fluorescence measurement at 932. The fluorescence spectrum is corrected for emission spectral response and the reference diode at 934. The A254 nm value is evaluated from the absorbance spectrum and if it exceeds the threshold saturation value an associated message is generated at 936. If no saturation warning is recorded, then the absorbance spectral data is used to apply the primary and secondary inner filter effect corrections to the fluorescence spectral data to achieve a correct fluorescence response at 938.

The fluorescence spectra from each detector are processed by calculating a cumulative integral curve where the total integral is normalized to unity at 940. The treated water signals from each step are subtracted from the source water signal to evaluate the effect of the associated treatment process at 942. The difference curve is evaluated in terms of area and wavelength peak and width to determine when the treatment process, which is a coagulation process in one representative embodiment, has had the desired effect 944. The cumulative integrals and difference curve data are further processed with the A254 nm value using the previously described wavelength coordinate evaluations and equations at 946 to provide the raw signal data parameters used to calculate/calibrate the total dissolved organic carbon (DOC) equivalent.

As also shown in FIG. 9, the cumulative integral signals are evaluated for component concentration ratios at 950 using one of several methods including but not limited to: classical least squares regression based on the sum of calibrated reference spectral contributions for each C1-C4 followed by calculation of the C2:C1 (or $C_{tot}$:C1) intensity ratio at 952. Residual sums can be evaluated to determine/detect and flag unknown contaminations or calibration issues by comparing them to a given threshold at 954. A restrained nonlinear regression can be applied to maintain the separate components but allow for slight deviations in peak widths and center parameters as represented at 956. The wavelength-intensity indices of the integral curves calibrated linearly against the C2:C1 ratio, noting, normally the C3 and C4 components have a very low relative contribution to the aromatic absorbance (extinction) at 254 nm compared to C1 and C2 as represented at 958. Also C3 and C4 usually have a statistically null relative response to coagulation thus excluding them from the term tends to improve the correlation between the C1 concentration and A254 nm.

The DOC is calculated using the multiple linear regression derived parameter coefficients x and y based on the independent A254 nm and C2:C1 (or $C_{tot}$:C1) intensity ratios, respectively as represented at 960 according to: DOC=x(A254 nm)*y (C2:C1), where x and y are linear coefficients, typically the regression is constrained to an intercept of 0 and slope of unity to increase the predictive correlation capacity and significance. The A254 nm and C2:C1 (or $C_{tot}$:$C_1$) signals would be calibrated using TOC meter data sampled in a batch mode comparison from the corresponding processing steps (locations) at corresponding times using the simple multiple linear regression (MLR) formula above to determine x and y for predictive capacity. The term y*(C2:C1) is linearly correlated by definition to the parameter more widely known as the specific UV absorbance coefficient (SUVA) since C2:C1 (or $C_{tot}$:$C_1$) represents the change in the relative component concentrations for the water samples which determines the linear relationship between A254 nm and DOC.

The linear analysis is based on recognition that the molar extinction coefficients for each component remain constant as a function of treatment such that the A254 nm changes only represent changes in the absolute and relative component concentration(s). In addition, the fluorescent quantum yields for each component also remain constant (both absolutely and in relation to each other) during treatment such that changes in the normalized fluorescence spectrum and integral shapes also only indicate relative changes in the component concentrations. Minor changes in quantum yield can be accounted for in the fluorescence spectral modeling when measured/detected as a function of the relationship between absorbance and fluorescence. Such changes may be associated with pH, temperature, and dissolved oxygen concentration.

As previously described, the A254 nm and the C2:C1 or ($C_{tot}$:C1) ratio can also be used to accurately predict disinfection byproduct formation potential in a multiple linear regression scheme potentially including several variables measured with other corresponding meters in the plant operation. Correlated/determinant parameters can include, but would not be limited to, chlorine dose and residual, contact times, temperature, pH, alkalinity and turbidity. A typical trihalomethane formation potential prediction (THMFP) equations is defined as:

$$THMFP(ppb) = a(A254\ nm) + b(C2:C1) + c(pH) + d([Cl-]) + e(T) + f([Alk])$$

where a, b, c, d, and e are linear coefficients. Typically, as with the TOC prediction, an intercept of 0 and slope of unity can be constrained in the linear equation fit parameters to increase the predictive correlation.

As those of ordinary skill in the art will appreciate, representative embodiments previously described may use a ratio of components, such as C2:C1 or C1:C2. Alternatively, or in combination, component concentrations, component values, or other parameters that correlate with the component concentrations or values may be used depending on the particular application and implementation. For example, the peak height associated with a particular component can be used as previously described. Furthermore, various embodiments do not require measurement of the emission spectra or dispersing of the emitted light. Rather, a diode may be used as the detector with acceptable results for some applications. Similarly, IFE correction may not be required in some applications.

As such, various embodiments of a water treatment or similar process monitor according to the present disclosure may provide savings or reduced use of associated treatment chemicals, such as coagulation chemicals and granulated activated carbon (on the order of tens of thousands of dollars per month for a typical application). Similarly, various embodiments may provide savings or reduced use of Biologically Activated Carbon (bGAC) in terms of activity needed to remove DOC. Likewise, embodiments may reduce membrane fouling and associated pumping energy as well as reducing membrane damage and increasing membrane useful life for Reverse Osmosis (RO), Forward Osmosis (FO), Membrane Bioreactors (MBR), Microfiltration (MF) and Ultrafiltration (UF) applications. Online monitoring of water treatment parameters according to various embodiments may be used for optimization of ozone treatment and reduction in taste and odor objections. Furthermore, various embodiments may be used to improve detection of organic contaminants including oil.

While exemplary embodiments are described above, it is not intended that these embodiments describe all possible forms of a system or method for analyzing a sample to determine a water treatment parameter or indicator according to the present disclosure. Rather, the words used in the specification are words of description rather than limitation, and it is understood that various changes may be made without departing from the spirit and scope of the disclosure. As previously described, the features of various representative embodiments may be combined in ways that are not explicitly illustrated or described to form further embodiments. While various embodiments may have been described as providing advantages or being preferred over other embodiments with respect to one or more desired characteristics, as one of ordinary skill in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, operation, etc. Any embodiments described herein as less desirable than other embodiments or prior art implementations with respect to one or more characteristics are not outside the scope of the disclosure and may be desirable for particular applications.

What is claimed is:

1. A system configured to measure absorbance and fluorescence of a sample, comprising:
    an input light source configured to generate at least one excitation wavelength;
    a chamber positioned to receive the sample and to be illuminated by the at least one excitation wavelength from the input light source;
    a single detector positioned to selectively receive and detect light transmitted through the sample during an absorbance measurement, and emitted by the sample along a non-parallel excitation optical path during a fluorescence measurement in response to illumination by each of the at least one excitation wavelength; and
    an optical fiber positioned to receive light transmitted through the sample and direct the transmitted light to the single detector during the absorbance measurement;
    wherein the light emitted by the sample during the fluorescence measurement is directed to the single detector without passing through any optical fiber.

2. The system of claim 1 further comprising an order sorting filter positioned upstream of the detector.

3. The system of claim 1 wherein the input light source generates light having a nominal wavelength of 254 nm.

4. The system of claim 3 wherein the input light source comprises:
    a broadband light source; and
    a narrowband filter passing light having a nominal wavelength of 254 nm.

5. The system of claim 1 wherein the input light source comprises:
    a plurality of monochromatic light sources each having different output wavelengths;
    an optical fiber associated with each of the plurality of light sources to selectively couple one of the plurality of light sources to an output of the input light source.

6. The system of claim 5 wherein the output of the input light source comprises an optical fiber.

7. The system of claim 5 further comprising:
    a reference detector coupled to the output of the input light source by an optical fiber.

8. The system of claim 1 further comprising:
    a computer in communication with the detector configured to correct the fluorescence measurement using the absorbance measurement, and to determine a sample parameter based on the fluorescence and absorbance measurements of the sample;
    wherein the computer is configured to take a first peak emission wavelength measurement of the sample and at least a second peak emission wavelength measurement of the sample emitted in response to the at least one excitation wavelength and to calculate the sample parameter based on the first and second peak emission wavelength measurements.

9. The system of claim 1 wherein the sample chamber comprises a flow-through cuvette with the sample flowing through the cuvette during the fluorescence and absorbance measurements.

10. The system of claim 1 wherein the sample chamber comprises a flow-through cuvette, the system further comprising at least one computer controlled valve to selectively stop flow through the cuvette during the fluorescence and absorbance measurements.

11. The system of claim 1 further comprising a beamsplitter positioned to combine an optical path of light transmitted by the sample during the absorbance measurement with light emitted by the sample during the fluorescence measurement upstream of the detector.

12. A system for monitoring a process using fluorescence and absorbance measurements, comprising:
  an input light source configured to generate at least one excitation wavelength;
  a sample chamber positioned to selectively receive pre-process and post-process samples and to be illuminated by the at least one excitation wavelength from the input light source;
  a single detector positioned to selectively receive and detect multiple wavelengths of light transmitted through a test sample in the sample chamber during an absorbance measurement, and emitted by the test sample during a fluorescence measurement in response to illumination by each of the at least one excitation wavelength, wherein the test sample is one of the pre-process and post-process samples;
  an optical fiber positioned to deliver light transmitted through the sample chamber during the absorbance measurement to the single detector; and
  optics positioned to receive light emitted by the test sample during the fluorescence measurement and deliver the light to the single detector without passing through any optical fiber.

13. The system of claim 12 further comprising:
  a computer in communication with the detector configured to correct the fluorescence measurement using the absorbance measurement and determine a pre-process value for a water treatment parameter and a post-process value for the water treatment parameter in response to the fluorescence and absorbance measurements of the pre-process and post-process samples; and
  a reference detector in communication with the computer and positioned to receive a portion of the at least one excitation wavelength, wherein the computer corrects the fluorescence and absorbance measurements based on a signal from the reference detector.

14. The system of claim 12 further comprising plumbing coupled to the sample chamber to deliver the pre-process and post-process samples.

15. The system of claim 14 wherein the plumbing comprises a computer controlled valve to control flow of the pre-process and post-process samples to the sample chamber.

* * * * *